(12) United States Patent
Ratti et al.

(10) Patent No.: US 6,248,563 B1
(45) Date of Patent: Jun. 19, 2001

(54) *CHLAMYDIA TRACHOMATIS* SEROTYPE D GENES

(75) Inventors: Giulio Ratti; Maurizio Comanducci; Mario F. Tecce; Marzia M. Giuliani, all of Siena (IT)

(73) Assignee: Scalvo SpA (IT)

( * ) Notice: Subject to any disclaimer, the term of this patent is extended or adjusted under 35 U.S.C. 154(b) by 0 days.

(21) Appl. No.: 08/468,544

(22) Filed: Jun. 6, 1995

Related U.S. Application Data

(62) Division of application No. 08/444,185, filed on May 18, 1995, which is a continuation of application No. 08/180,528, filed on Jan. 12, 1994, now abandoned, which is a division of application No. 07/991,512, filed on Dec. 17, 1992, now abandoned, which is a continuation of application No. 07/661,820, filed on Feb. 28, 1991, now abandoned.

(30) Foreign Application Priority Data

Feb. 7, 1991 (IT) .............................................. MI91A0314

(51) Int. Cl.$^7$ ............................. C12P 21/06; C12P 21/04; A61K 39/118; C07H 19/00
(52) U.S. Cl. .................... 435/69.3; 424/263.1; 435/69.1; 435/69.7; 435/71.1; 435/320.1; 536/22.1; 536/23.1; 536/23.7
(58) Field of Search .................. 536/22.1, 23.1, 536/23.4, 23.7; 435/69.1, 69.3, 69.7, 71.1, 252.33, 320.1; 424/263.1

(56) References Cited

FOREIGN PATENT DOCUMENTS

0336412 * 10/1989 (EP) ................................ C12Q/1/68

OTHER PUBLICATIONS

Comanducci et al Plasmid 23:149–150, 1990.*
Comanducci et al International Symposium on Human Chlamydial Infectious, pp. 121–124, 1990 Database Search.*
Comanducci et al Molecular Microbiology 2:531–538, 1988.*
Hatt et al Nucleic Acids Research vol. 16 pp 4053–4067, 1988.*
Attached data Base Search.*

* cited by examiner

*Primary Examiner*—Rodney P. Swartz
(74) *Attorney, Agent, or Firm*—Woodcock Washburn Kurtz Mackiewicz & Norris LLP; Alisa Harbin; Robert P. Blackburn

(57) ABSTRACT

A plasmid isolated from *Clamydia trachomatis* is described, which comprises 8 genes encoding proteins useful in the formulation of vaccines or diagnostic test for determining the bacterium or specific antibodies generated during *C. trachomatis* infections; in particular the recombinant fusion MS2-pgp3D protein is described comprising polypeptidic sequences encoded by pCT and immunogenic in the course of infections in man. A method for preparing said protein in *E. coli* further described.

9 Claims, 13 Drawing Sheets

FIG. 1A (1)

```
          10                    30                    50
ATATTCATATTCTGTTGCCAGAAAAAACACCTTTAGGCTATATTAGAGCCATCTTCTTTG 70                    90                   110
AAGCGTTGTCTTCTCGAGAAGATTTATCGTACGCAAATATCATCTTTGCGGTTGCGTGTC 130                   150                   170
CTGTGACCTTCATTATGTCGGAGTCTGAGCACCCTAGGCGTTTGTACTCCGTCACAGCGG 190                   210                   230
TTGCTCGAAGCACGTGCGGGGTTATTTTAAAAGGGATTGCAGCTTGTAGTCCTGCTTGAG 250                   270                   290
AGAACGTGCGGGCGATTTGCCTTAACCCCACCATTTTTCCGGAGCGAGTTACGAAGACAA 310                   330                   350
AACCTCTTCGTTGACCGATGTACTCTTGTAGAAAGTGCATAAACTTCTGAGGATAAGTTA 370                   390                   410
TAATAATCCTCTTTTCTGTCTGACGGTTCTTAAGCTGGGAGAAAGAAATGGTAGCTTGTT 430                   450                   470
GGAAACAAATCTGACTAATCTCCAAGCTTAAGACTTCAGAGGAGCGTTTACCTCCTTGGA 490                   510                   530
GCATTGTCTGGGCGATCAACCAATCCCGGGCATTGATTTTTTTAGCTCTTTTAGGAAGG 550                   570                   590
ATGCTGTTTGCAAACTGTTCATCGCATCCGTTTTACTATTTCCTGGTTTTAAAAAATG 610                   630                   650
TTCGACTATTTCTTGTTTAGAAGGTTGCGCTATAGCGACTATTCCTTGAGTCATCCTGT 670                   690                   710
TTAGGAATCTTGTTAAGGAAATATAGCTTGCTGCTCGAACTTGTTTAGTACCTTCGGTCC 730                   750                   770
AAGAAGTCTTGGCAGAGGAAACTTTTTTAATCGCATCTAGGATTAGATTATGATTTAAAA 790                   810                   830
GGGAAAACTCTTGCAGATTCATATCCAAGGACAATAGACCAATCTTTTCTAAAGACAAAA 850                   870                   890
AAGATCCTCGATATGATCTACAAGTATGTTTGTTGAGTGATGCGGTCCAATGCATAATAA 910                   930                   950
CTTCGAATAAGGAGAAGCTTTTCATGCGTTTCCAATAGGATTCTTGGCGAATTTTAAAA 970                   990                  1010
CTTCCTGATAAGACTTTTCACTATATTCTAACGACATTTCTTGCTGCAAAGATAAAATCC 1030                  1050                  1070
CTTTACCCATGAAATCCCTCGTGATATAACCTATCCGTAAAATGTCCTGATTAGTGAAAT 1090                  1110                  1130
AATCAGGTTGTTAACAGGATAGCACGCTCGGTATTTTTTATATAAACATGAAAACTCGT
                                          ORF1 >>  MetLysThrArg
```

FIG. 1A (2)

```
       1150                   1170                   1190
TCCGAAATAGAAAATCGCATGCAAGATATCGAGTATGCGTTGTTAGGTAAAGCTCTGATA
SerGluIleGluAsnArgMetGlnAspIleGluTyrAlaLeuLeuGlyLysAlaLeuIle 1210                   1230                   1250
TTTGAAGACTCTACTGAGTATATTCTGAGGCAGCTTGCTAATTATGAGTTTAAGTGTTCT
PheGluAspSerThrGluTyrIleLeuArgGlnLeuAlaAsnTyrGluPheLysCysSer 1270                   1290                   1310
CATCATAAAAACATATTCATAGTATTTAAACACTTAAAAGACAATGGATTACCTATAACT
HisHisLysAsnIlePheIleValPheLysHisLeuLysAspAsnGlyLeuProIleThr 1330                   1350                   1370
GTAGACTCGGCTTGGGAAGAGCTTTTGCGGCGTCGTATCAAAGATATGGACAAATCGTAT
ValAspSerAlaTrpGluGluLeuLeuArgArgArgIleLysAspMetAspLysSerTyr 1390                   1410                   1430
CTCGGGTTAATGTTGCATGATGCTTTATCAAATGACAAGCTTAGATCCGTTTCTCATACG
LeuGlyLeuMetLeuHisAspAlaLeuSerAsnAspLysLeuArgSerValSerHisThr 1450                   1470                   1490
GTTTTCCTCGATGATTTGAGCGTGTGTAGCGCTGAAGAAAATTTGAGTAATTTCATTTTC
ValPheLeuAspAspLeuSerValCysSerAlaGluGluAsnLeuSerAsnPheIlePhe 1510                   1530                   1550
CGCTCGTTTAATGAGTACAATGAAAATCCATTGCGTAGATCTCCGTTTCTATTGCTTGAG
ArgSerPheAsnGluTyrAsnGluAsnProLeuArgArgSerProPheLeuLeuLeuGlu 1570                   1590                   1610
CGTATAAAGGGAAGGCTTGATAGTGCTATAGCAAAGACTTTTTCTATTCGCAGCGCTAGA
ArgIleLysGlyArgLeuAspSerAlaIleAlaLysThrPheSerIleArgSerAlaArg 1630                   1650                   1670
GGCCGGTCTATTTATGATATATTCTCACAGTCAGAAATTGGAGTGCTGGCTCGTATAAAA
GlyArgSerIleTyrAspIlePheSerGlnSerGluIleGlyValLeuAlaArgIleLys 1690                   1710                   1730
AAAAGACGAGTAGCGTTCTCTGAGAATCAAAATTCTTTCTTTGATGGCTTCCCAACAGGA
LysArgArgValAlaPheSerGluAsnGlnAsnSerPhePheAspGlyPheProThrGly 1750                   1770                   1790
TACAAGGATATTGATGATAAAGGAGTTATCTTAGCTAAAGGTAATTTCGTGATTATAGCA
TyrLysAspIleAspAspLysGlyValIleLeuAlaLysGlyAsnPheValIleIleAla 1810                   1830                   1850
GCTAGACCATCTATAGGGAAAACAGCTTTAGCTATAGACATGGCGATAAATCTTGCGGTT
AlaArgProSerIleGlyLysThrAlaLeuAlaIleAspMetAlaIleAsnLeuAlaVal 1870                   1890                   1910
ACTCAACAGCGTAGAGTTGGTTTCCTATCTCTAGAAATGAGCGCAGGTCAAATTGTTGAG
ThrGlnGlnArgArgValGlyPheLeuSerLeuGluMetSerAlaGlyGlnIleValGlu 1930                   1950                   1970
CGGATTATTGCTAATTTAACAGGAATATCTGGTGAAAAATTACAAAGAGGGGATCTCTCT
ArgIleIleAlaAsnLeuThrGlyIleSerGlyGluLysLeuGlnArgGlyAspLeuSer
```

FIG. 1A (3)

```
         1990                2010                2030
AAAGAAGAATTATTCCGAGTAGAAGAAGCTGGAGAAACGGTTAGAGAATCACATTTTTAT
LysGluGluLeuPheArgValGluGluAlaGlyGluThrValArgGluSerHisPheTyr 2050                2070                2090
ATCTGCAGTGATAGTCAGTATAAGCTTAACTTAATCGCGAATCAGATCCGGTTGCTGAGA
IleCysSerAspSerGlnTyrLysLeuAsnLeuIleAlaAsnGlnIleArgLeuLeuArg 2110                2130                2150
AAAGAAGATCGAGTAGACGTAATATTTATCGATTACTTGCAGTTGATCAACTCATCGGTT
LysGluAspArgValAspValIlePheIleAspTyrLeuGlnLeuIleAsnSerSerVal 2170                2190                2210
GGAGAAAATCGTCAAAATGAAATAGCAGATATATCTAGAACCTTAAGAGGTTTAGCCTCA
GlyGluAsnArgGlnAsnGluIleAlaAspIleSerArgThrLeuArgGlyLeuAlaSer 2230                2250                2270
GAGCTAAACATTCCTATAGTTTGTTTATCCCAACTATCTAGAAAAGTTGAGGATAGAGCA
GluLeuAsnIleProIleValCysLeuSerGlnLeuSerArgLysValGluAspArgAla 2290                2310                2330
AATAAAGTTCCCATGCTTTCAGATTTGCGAGACAGCGGTCAAATAGAGCAAGACGCAGAT
AsnLysValProMetLeuSerAspLeuArgAspSerGlyGlnIleGluGlnAspAlaAsp 2350                2370                2390
GTGATTTTGTTTATCAATAGGAAGGAATCGTCTTCTAATTGTGAGATAACTGTTGGGAAA
ValIleLeuPheIleAsnArgLysGluSerSerSerAsnCysGluIleThrValGlyLys 2410                2430                2450
AATAGACATGGATCGGTTTTCTCTTCGGTATTACATTTCGATCCAAAAATTAGTAAATTC
AsnArgHisGlySerValPheSerSerValLeuHisPheAspProLysIleSerLysPhe 2470                2490                2510
TCCGCTATTAAAAAAGTATGGTAAATTATAGTAACTGCCACTTCATCAAAAGTCCTATCC
SerAlaIleLysLysValTrpEnd
         ORF2 >> MetValAsnTyrSerAsnCysHisPheIleLysSerProIleH 2530                2550                2570
ACCTTGAAAATCAGAAGTTTGGAAGAAGACCTGGTCAATCTATTAAGATATCTCCCAAAT
isLeuGluAsnGlnLysPheGlyArgArgProGlyGlnSerIleLysIleSerProLysL 2590                2610                2630
TGGCTCAAAATGGGATGGTAGAAGTTATAGGTCTTGATTTTCTTTCATCTCATTACCATG
euAlaGlnAsnGlyMetValGluValIleGlyLeuAspPheLeuSerSerHisTyrHisA 2650                2670                2690
CATTAGCAGCTATCCAAAGATTACTGACCGCAACGAATTACAAGGGGAACACAAAAGGGG
laLeuAlaAlaIleGlnArgLeuLeuThrAlaThrAsnTyrLysGlyAsnThrLysGlyV 2710                2730                2750
TTGTTTTATCCAGAGAATCAAATAGTTTTCAATTTGAAGGATGGATACCAAGAATCCGTT
alValLeuSerArgGluSerAsnSerPheGlnPheGluGlyTrpIleProArgIleArgP 2770                2790                2810
TTACAAAAACTGAATTCTTAGAGGCTTATGGAGTTAAGCGGTATAAAACATCCAGAAATA
heThrLysThrGluPheLeuGluAlaTyrGlyValLysArgTyrLysThrSerArgAsnL
```

FIG. 1A (4)

```
                 2830                    2850                    2870
      AGTATGAGTTTAGTGGAAAAGAAGCTGAAACTGCTTTAGAAGCCTTATACCATTTAGGAC
      ysTyrGluPheSerGlyLysGluAlaGluThrAlaLeuGluAlaLeuTyrHisLeuGlyH 2890                    2910                    2930
      ATCAACCGTTTTTAATAGTGGCAACTAGAACTCGATGGACTAATGGAACACAAATAGTAG
      isGlnProPheLeuIleValAlaThrArgThrArgTrpThrAsnGlyThrGlnIleValA 2950                    2970                    2990
      ACCGTTACCAAACTCTTTCTCCGATCATTAGGATTTACGAAGGATGGGAAGGTTTAACTG
      spArgTyrGlnThrLeuSerProIleIleArgIleTyrGluGlyTrpGluGlyLeuThrA 3010                    3030                    3050
      ACGAAGAAAATATAGATATAGACTTAACACCTTTTAATTCACCACCTACACGGAAACATA
      spGluGluAsnIleAspIleAspLeuThrProPheAsnSerProProThrArgLysHisL 3070                    3090                    3110
      AAGGGTTCGTTGTAGAGCCATGTCCTATCTTGGTAGATCAAATAGAATCCTACTTTGTAA
      ysGlyPheValValGluProCysProIleLeuValAspGlnIleGluSerTyrPheValI 3130                    3150                    3170
      TCAAGCCTGCAAATGTATACCAAGAAATAAAAATGCGTTTCCCAAATGCATCAAAGTATG
      leLysProAlaAsnValTyrGlnGluIleLysMetArgPheProAsnAlaSerLysTyrA 3190                    3210                    3230
      CTTACACATTTATCGACTGGGTGATTACAGCAGCTGCGAAAAAGAGACGAAAATTAACTA
      laTyrThrPheIleAspTrpValIleThrAlaAlaAlaLysLysArgArgLysLeuThrL 3250                    3270                    3290
      AGGATAATTCTTGGCCAGAAAACTTGTTATTAAACGTTAACGTTAAAAGTCTTGCATATA
      ysAspAsnSerTrpProGluAsnLeuLeuLeuAsnValAsnValLysSerLeuAlaTyrI 3310                    3330                    3350
      TTTTAAGGATGAATCGGTACATCTGTACAAGGAACTGGAAAAAAATCGAGTTAGCTATCG
      leLeuArgMetAsnArgTyrIleCysThrArgAsnTrpLysLysIleGluLeuAlaIleA 3370                    3390                    3410
      ATAAATGTATAGAAATCGCCATTCAGCTTGGCTGGTTATCTAGAAGAAAACGCATTGAAT
      spLysCysIleGluIleAlaIleGlnLeuGlyTrpLeuSerArgArgLysArgIleGluP 3430                    3450                    3470
      TTCTGGATTCTTCTAAACTCTCTAAAAAAGAAATTCTATATCTAAATAAAGAGCGCTTTG
      heLeuAspSerSerLysLeuSerLysLysGluIleLeuTyrLeuAsnLysGluArgPheG 3490                    3510                    3530
      AAGAAATAACTAAGAAATCTAAAGAACAAATGGAACAATTAGAACAAGAATCTATTAATT
      luGluIleThrLysLysSerLysGluGlnMetGluGlnLeuGluGlnGluSerIleAsnE 3550                    3570                    3590
      AATAGCAAGCTTGAAACTAAAAACCTAATTTATTTAAAGCTCAAAATAAAAAGAGTTTT
      nd                                                         ORF3

3610                    3630                    3650
      AAAATGGGAAATTCTGGTTTTTATTTGTATAACACTGAAAACTGCGTCTTTGCTGATAAT
        >>MetGlyAsnSerGlyPheTyrLeuTyrAsnThrGluAsnCysValPheAlaAspAsn 3670                    3690                    3710
      ATCAAAGTTGGGCAAATGACAGAGCCGCTCAAGGACCAGCAAATAATCCTTGGGACAACA
      IleLysValGlyGlnMetThrGluProLeuLysAspGlnGlnIleIleLeuGlyThrThr
```

FIG. 1A (5)

```
             3730              3750                   3770
TCAACACCTGTCGCAGCCAAAATGACAGCTTCTGATGGAATATCTTTAACAGTCTCCAAT
SerThrProValAlaAlaLysMetThrAlaSerAspGlyIleSerLeuThrValSerAsn 3790              3810                   3830
AATTCATCAACCAATGCTTCTATTACAATTGGTTTGGATGCGGAAAAAGCTTACCAGCTT
AsnSerSerThrAsnAlaSerIleThrIleGlyLeuAspAlaGluLysAlaTyrGlnLeu 3850              3870                   3890
ATTCTAGAAAAGTTGGGAGATCAAATTCTTGATGGAATTGCTGATACTATTGTTGATAGT
IleLeuGluLysLeuGlyAspGlnIleLeuAspGlyIleAlaAspThrIleValAspSer 3910              3930                   3950
ACAGTCCAAGATATTTTAGACAAAATCAAAACAGACCCTTCTCTAGGTTTGTTGAAAGCT
ThrValGlnAspIleLeuAspLysIleLysThrAspProSerLeuGlyLeuLeuLysAla 3970              3990                   4010
TTTAACAACTTTCCAATCACTAATAAAATTCAATGCAACGGGTTATTCACTCCCAGTAAC
PheAsnAsnPheProIleThrAsnLysIleGlnCysAsnGlyLeuPheThrProSerAsn 4030              4050                   4070
ATTGAAACTTTATTAGGAGGAACTGAAATAGGAAAATTCACAGTCACACCCAAAAGCTCT
IleGluThrLeuLeuGlyGlyThrGluIleGlyLysPheThrValThrProLysSerSer 4090              4110                   4130
GGGAGCATGTTCTTAGTCTCAGCAGATATTATTGCATCAAGAATGGAAGGCGGCGTTGTT
GlySerMetPheLeuValSerAlaAspIleIleAlaSerArgMetGluGlyGlyValVal 4150              4170                   4190
CTAGCTTTGGTACGAGAAGGTGATTCTAAGCCCTGCGCGATTAGTTATGGATACTCATCA
LeuAlaLeuValArgGluGlyAspSerLysProCysAlaIleSerTyrGlyTyrSerSer 4210              4230                   4250
GGCATTCCTAATTTATGTAGTCTAAGAACCAGTATTACTAATACAGGATTGACTCCGACA
GlyIleProAsnLeuCysSerLeuArgThrSerIleThrAsnThrGlyLeuThrProThr 4270              4290                   4310
ACGTATTCATTACGTGTAGGCGGTTTAGAAAGCGGTGTGGTATGGGTTAATGCCCTTTCT
ThrTyrSerLeuArgValGlyGlyLeuGluSerGlyValValTrpValAsnAlaLeuSer 4330              4350                   4370
AATGGCAATGATATTTTAGGAATAACAAATACTTCTAATGTATCTTTTTTAGAGGTAATA
AsnGlyAsnAspIleLeuGlyIleThrAsnThrSerAsnValSerPheLeuGluValIle 4390              4410                   4430
CCTCAAACAACGCTTAAACAATTTTTATTGGATTTTCTTATAGGTTTTATATTTAGAG
ProGlnThrAsnAlaEnd 4450              4470                   4490
AAAACAGTTCGAATTACGGGGTTTGTTATGCAAAATAAAAGAAAGTGAGGGACGATTTT
                  ORF4 >> MetGlnAsnLysArgLysValArgAspAspPhe 4510              4530                   4550
ATTAAAATTGTTAAAGATGTGAAAAAAGATTTCCCCGAATTAGACCTAAAAATACGAGTA
IleLysIleValLysAspValLysLysAspPheProGluLeuAspLeuLysIleArgVal 4570              4590                   4610
AACAAGGAAAAAGTAACTTTCTTAAATTCTCCCTTAGAACTCTACCATAAAAGTGTCTCA
AsnLysGluLysValThrPheLeuAsnSerProLeuGluLeuTyrHisLysSerValSer
```

FIG. 1A (6)

```
          4630                 4650                  4670
CTAATTCTAGGACTGCTTCAACAAATAGAAAACTCTTTAGGATTATTCCCAGACTCTCCT
LeuIleLeuGlyLeuLeuGlnGlnIleGluAsnSerLeuGlyLeuPheProAspSerPro 4690                 4710                  4730
GTTCTTGAAAAATTAGAGGATAACAGTTTAAAGCTAAAAAAGGCTTTGATTATGCTTATC
ValLeuGluLysLeuGluAspAsnSerLeuLysLeuLysLysAlaLeuIleMetLeuIle 4750                 4770                  4790
TTGTCTAGAAAAGACATGTTTTCCAAGGCTGAATAGACAACTTACTCTAACGTTGGAGTT
LeuSerArgLysAspMetPheSerLysAlaGluEnd                     ORF5

4810                 4830                  4850
GATTTGCACACCTTAGTTTTTTGCTCTTTTAAGGGAGGAACTGGAAAAACAACACTTTCT
>>  LeuHisThrLeuValPheCysSerPheLysGlyGlyThrGlyLysThrThrLeuSer 4870                 4890                  4910
CTAAACGTGGGATGCAACTTGGCCCAATTTTTAGGGAAAAAAGTGTTACTTGCTGACCTA
LeuAsnValGlyCysAsnLeuAlaGlnPheLeuGlyLysLysValLeuLeuAlaAspLeu 4930                 4950                  4970
GACCCGCAATCCAATTTATCTTCTGGATTGGGGGCTAGTGTCAGAAGTGACCAAAAAGGC
AspProGlnSerAsnLeuSerSerGlyLeuGlyAlaSerValArgSerAspGlnLysGly 4990                 5010                  5030
TTGCACGACATAGTATACACATCAAACGATTTAAAATCAATCATTTGCGAAACAAAAAAA
LeuHisAspIleValTyrThrSerAsnAspLeuLysSerIleIleCysGluThrLysLys 5050                 5070                  5090
GATAGTGTGGACCTAATTCCTGCATCATTTTCATCCGAACAGTTTAGAGAATTGGATATT
AspSerValAspLeuIleProAlaSerPheSerSerGluGlnPheArgGluLeuAspIle 5110                 5130                  5150
CATAGAGGACCTAGTAACAACTTAAAGTTATTTCTGAATGAGTACTGCGCTCCTTTTTAT
HisArgGlyProSerAsnAsnLeuLysLeuPheLeuAsnGluTyrCysAlaProPheTyr 5170                 5190                  5210
GACATCTGCATAATAGACACTCCACCTAGCCTAGGAGGGTTAACGAAAGAAGCTTTTGTT
AspIleCysIleIleAspThrProProSerLeuGlyGlyLeuThrLysGluAlaPheVal 5230                 5250                  5270
GCAGGAGACAAATTAATTGCTTGTTTAACTCCAGAACCTTTTTCTATTCTAGGGTTACAA
AlaGlyAspLysLeuIleAlaCysLeuThrProGluProPheSerIleLeuGlyLeuGln 5290                 5310                  5330
AAGATACGTGAATTCTTAAGTTCGGTCGGAAAACCTGAAGAAGAACACATTCTTGGAATA
LysIleArgGluPheLeuSerSerValGlyLysProGluGluGluHisIleLeuGlyIle 5350                 5370                  5390
GCTTTGTCTTTTTGGGATGATCGTAACTCGACTAACCAAATGTATATAGACATTATCGAG
AlaLeuSerPheTrpAspAspArgAsnSerThrAsnGlnMetTyrIleAspIleIleGlu 5410                 5430                  5450
TCTATTTACAAAAACAAGCTTTTTTCAACAAAAATTCGTCGAGATATTTCTCTCAGCCGT
SerIleTyrLysAsnLysLeuPheSerThrLysIleArgArgAspIleSerLeuSerArg 5470                 5490                  5510
TCTCTTCTTAAAGAAGATTCTGTAGCTAATGTCTATCCAAATTCTAGGGCCGCAGAAGAT
SerLeuLeuLysGluAspSerValAlaAsnValTyrProAsnSerArgAlaAlaGluAsp
```

FIG. 1A (7)

```
            5530                  5550                  5570
ATTCTGAAGTTAACGCATGAAATAGCAAATATTTTGCATATCGAATATGAACGAGATTAC
IleLeuLysLeuThrHisGluIleAlaAsnIleLeuHisIleGluTyrGluArgAspTyr 5590                  5610                  5630
TCTCAGAGGACAACGTGAACAAACTAAAAAAGAAGCGGATGTCTTTTTTAAAAAAAATC
SerGlnArgThrThrEnd
        ORF6 >> ValAsnLysLeuLysLysGluAlaAspValPhePheLysLysAspG 5650                  5670                  5690
AAACTGCCGCTTCTCTAGATTTTAAGAAGACGCTTCCCTCCATTGAACTATTCTCAGCAA
 lnThrAlaAlaSerLeuAspPheLysLysThrLeuProSerIleGluLeuPheSerAlaT 5710                  5730                  5750
CTTTGAATTCTGAGGAAAGTCAGAGTTTGGATCGATTATTTTTATCAGAGTCCCAAAACT
hrLeuAsnSerGluGluSerGlnSerLeuAspArgLeuPheLeuSerGluSerGlnAsnT 5770                  5790                  5810
ATTCGGATGAAGAATTTTATCAAGAAGACATCCTAGCGGTAAAACTGCTTACTGGTCAGA
yrSerAspGluGluPheTyrGlnGluAspIleLeuAlaValLysLeuLeuThrGlyGlnI 5830                  5850                  5870
TAAAATCCATACAGAAGCAACACGTACTTCTTTTAGGAGAAAAAATCTATAATGCTAGAA
leLysSerIleGlnLysGlnHisValLeuLeuLeuGlyGluLysIleTyrAsnAlaArgL 5890                  5910                  5930
AAATCCTGAGTAAGGATCACTTCTCCTCAACAACTTTTTCATCTTGGATAGAGTTAGTTT
ysIleLeuSerLysAspHisPheSerSerThrThrPheSerSerTrpIleGluLeuValP 5950                  5970                  5990
TTAGAACTAAGTCTTCTGCTTACAATGCTCTTGCATATTACGAGCTTTTTATAAACCTCC
heArgThrLysSerSerAlaTyrAsnAlaLeuAlaTyrTyrGluLeuPheIleAsnLeuP 6010                  6030                  6050
CCAACCAAACTCTACAAAAAGAGTTTCAATCGATCCCCTATAAATCCGCATATATTTTGG
roAsnGlnThrLeuGlnLysGluPheGlnSerIleProTyrLysSerAlaTyrIleLeuA 6070                  6090                  6110
CCGCTAGAAAAGGCGATTTAAAAACCAAGGTCGATGTGATAGGGAAAGTATGTGGAATGT
laAlaArgLysGlyAspLeuLysThrLysValAspValIleGlyLysValCysGlyMetS 6130                  6150                  6170
CGAACTCATCGGCGATAAGGGTGTTGGATCAATTTCTTCCTTCATCTAGAAACAAAGACG
erAsnSerSerAlaIleArgValLeuAspGlnPheLeuProSerSerArgAsnLysAspV 6190                  6210                  6230
TTAGAGAAACGATAGATAAGTCTGATTCAGAGAAGAATCGCCAATTATCTGATTTCTTAA
alArgGluThrIleAspLysSerAspSerGluLysAsnArgGlnLeuSerAspPheLeuI 6250                  6270                  6290
TAGAGATACTTCGCATCATGTGTTCCGGAGTTTCTTTGTCCTCCTATAACGAAAATCTTC
leGluIleLeuArgIleMetCysSerGlyValSerLeuSerSerTyrAsnGluAsnLeuL 6310                  6330                  6350
TACAACAGCTTTTTGAACTTTTTAAGCAAAAGAGCTGATCCTCCGTCAGCTCATATATAT
euGlnGlnLeuPheGluLeuPheLysGlnLysSerEnd
```

FIG. 1A (8)

```
                6370                  6390                  6410
ATATCTATTATATATATATTTAGGGATTTGATTTCACGAGAGAGATTTGCAACTCTTG 6430                  6450                  6470
GTGGTAGACTTTGCAACTCTTGGTGGTAGACTTTGCAACTCTTGGTGGTAGACTTTGCAA 6490                  6510                  6530
CTCTTGGTGGTAGACTTGGTCATAATGGACTTTTGTTAAAAAATTTATTAAAATCTTAGA 6550                  6570                  6590
GCTCCGATTTTGAATAGCTTTGGTTAAGAAAATGGGCTCGATGGCTTTCCATAAAAGTAG
             ORF7 >>  LeuValLysLysMetGlySerMetAlaPheHisLysSerAr 6610                  6630                  6650
ATTGTTTTTAACTTTTGGGGACGCGTCGGAAATTTGGTTATCTACTTTATCTTATCTAAC
gLeuPheLeuThrPheGlyAspAlaSerGluIleTrpLeuSerThrLeuSerTyrLeuTh 6670                  6690                  6710
TAGAAAAAATTATGCGTCTGGGATTAACTTTCTTGTTTCTTTAGAGATTCTGGATTTATC
rArgLysAsnTyrAlaSerGlyIleAsnPheLeuValSerLeuGluIleLeuAspLeuSe 6730                  6750                  6770
GGAAACCTTGATAAAGGCTATTTCTCTTGACCACAGCGAATCTTTGTTTAAAATCAAGTC
rGluThrLeuIleLysAlaIleSerLeuAspHisSerGluSerLeuPheLysIleLysSe 6790                  6810                  6830
TCTAGATGTTTTTAATGGAAAAGTTGTTTCAGAGGCATCTAAACAGGCTAGAGCGGCATG
rLeuAspValPheAsnGlyLysValValSerGluAlaSerLysGlnAlaArgAlaAlaCy 6850                  6870                  6890
CTACATATCTTTCACAAAGTTTTTGTATAGATTGACCAAGGGATATATTAAACCCGCTAT
sTyrIleSerPheThrLysPheLeuTyrArgLeuThrLysGlyTyrIleLysProAlaIl 6910                  6930                  6950
TCCATTGAAAGATTTTGGAAACACTACATTTTTTAAAATCCGAGACAAAATCAAAACAGA
eProLeuLysAspPheGlyAsnThrThrPhePheLysIleArgAspLysIleLysThrGl 6970                  6990                  7010
ATCGATTTCTAAGCAGGAATGGACAGTTTTTTTTGAAGCGCTCCGGATAGTGAATTATAG
uSerIleSerLysGlnGluTrpThrValPhePheGluAlaLeuArgIleValAsnTyrAr 7030                  7050                  7070
AGACTATTTAATCGGTAAATTGATTGTACAAGGGATCCGTAAGTTAGACGAAATTTTGTC
gAspTyrLeuIleGlyLysLeuIleValGlnGlyIleArgLysLeuAspGluIleLeuSe 7090                  7110                  7130
TTTGCGCACAGACGATCTATTTTTTGCATCCAATCAGATTTCCTTTCGCATTAAAAAAAG
rLeuArgThrAspAspLeuPhePheAlaSerAsnGlnIleSerPheArgIleLysLysAr 7150                  7170                  7190
ACAGAATAAAGAAACCAAAATTCTAATCACATTTCCTATCAGCTTAATGGAAGAGTTGCA
gGlnAsnLysGluThrLysIleLeuIleThrPheProIleSerLeuMetGluGluLeuGl 7210                  7230                  7250
AAAATACACTTGTGGGAGAAATGGGAGAGTATTTGTTTCTAAAATAGGGATTCCTGTAAC
nLysTyrThrCysGlyArgAsnGlyArgValPheValSerLysIleGlyIleProValTh
```

FIG. 1A (9)

```
         7270                  7290                  7310
AACAAGTCAGGTTGCGCATAATTTTAGGCTTGCAGAGTTCCATAGTGCTATGAAAATAAA
rThrSerGlnValAlaHisAsnPheArgLeuAlaGluPheHisSerAlaMetLysIleLy 7330                  7350                  7370
AATTACTCCCAGAGTACTTCGTGCAAGCGCTTTGATTCATTTAAAGCAAATAGGATTAAA
sIleThrProArgValLeuArgAlaSerAlaLeuIleHisLeuLysGlnIleGlyLeuLy 7390                  7410                  7430
AGATGAGGAAATCATGCGTATTTCCTGTCTTTCATCGAGACAAAGTGTGTGTTCTTATTG
sAspGluGluIleMetArgIleSerCysLeuSerSerArgGlnSerValCysSerTyrCy 7450                  7470                  7490
TTCTGGGGAAGAGGTAATTCCTCTAGTACAAACACCCACAATATTGTGATATAATTAAAA
sSerGlyGluGluValIleProLeuValGlnThrProThrIleLeuEnd

TT
```

FIG. 1B (1)

GCATGCGATTTTCTATTTCGGAACGAGTTTTCATGTTTATATAAAAAAATACCGAGCGTG

CTATCCTGTTAACAACCTGATTATTTCACTAATCAGGACATTTTACGGATAGGTTATATC

ACGAGGGATTTCATGGGTAAAGGGATTTTATCTTTGCAGCAAGAAATGTCGTTAGAATAT
    ORF8 >> MetGlyLysGlyIleLeuSerLeuGlnGlnGluMetSerLeuGluTyr

AGTGAAAAGTCTTATCAGGAAGTTTTAAAAATTCGCCAAGAATCCTATTGGAAACGCATG
SerGluLysSerTyrGlnGluValLeuLysIleArgGlnGluSerTyrTrpLysArgMet

AAAAGCTTCTCCTTATTCGAAGTTATTATGCATTGGACCGCATCACTCAACAAACATACT
LysSerPheSerLeuPheGluValIleMetHisTrpThrAlaSerLeuAsnLysHisThr

TGTAGATCATATCGAGGATCTTTTTTGTCTTTAGAAAAGATTGGTCTATTGTCCTTGGAT
CysArgSerTyrArgGlySerPheLeuSerLeuGluLysIleGlyLeuLeuSerLeuAsp

ATGAATCTGCAAGAGTTTTCCCTTTTAAATCATAATCTAATCCTAGATGCGATTAAAAAA
MetAsnLeuGlnGluPheSerLeuLeuAsnHisAsnLeuIleLeuAspAlaIleLysLys

GTTTCCTCTGCCAAGACTTCTTGGACCGAAGGTACTAAACAAGTTCGAGCAGCAAGCTAT
ValSerSerAlaLysThrSerTrpThrGluGlyThrLysGlnValArgAlaAlaSerTyr

ATTTCCTTAACAAGATTCCTAAACAGGATGACTCAAGGAATAGTCGCTATAGCGCAACCT
IleSerLeuThrArgPheLeuAsnArgMetThrGlnGlyIleValAlaIleAlaGlnPro

TCTAAACAAGAAAATAGTCGAACATTTTTTAAAACCAGGGAAATAGTAAAAACGGATGCG
SerLysGlnGluAsnSerArgThrPhePheLysThrArgGluIleValLysThrAspAla

ATGAACAGTTTGCAAACAGCATCCTTCCTAAAAGAGCTAAAAAAAATCAATGCCCGGGAT
MetAsnSerLeuGlnThrAlaSerPheLeuLysGluLeuLysLysIleAsnAlaArgAsp

TGGTTGATCGCCCAGACAATGCTCCAAGGAGGTAAACGCTCCTCTGAAGTCTTAAGCTTG
TrpLeuIleAlaGlnThrMetLeuGlnGlyGlyLysArgSerSerGluValLeuSerLeu

GAGATTAGTCAGATTTGTTTCCAACAAGCTACCATTTCTTTCTCCCAGCTTAAGAACCGT
GluIleSerGlnIleCysPheGlnGlnAlaThrIleSerPheSerGlnLeuLysAsnArg

CAGACAGAAAAGAGGATTATTATAACTTATCCTCAGAAGTTTATGCACTTTCTACAAGAG
GlnThrGluLysArgIleIleIleThrTyrProGlnLysPheMetHisPheLeuGlnGlu

FIG. 1B (2)

```
TACATCGGTCAACGAAGAGGTTTTGTCTTCGTAACTCGCTCCGGAAAAATGGTGGGGTTA
TyrIleGlyGlnArgArgGlyPheValPheValThrArgSerGlyLysMetValGlyLeu

AGGCAAATCGCCCGCACGTTCTCTCAAGCAGGACTACAAGCTGCAATCCCTTTTAAAATA
ArgGlnIleAlaArgThrPheSerGlnAlaGlyLeuGlnAlaAlaIleProPheLysIle

ACCCCGCACGTGCTTCGAGCAACCGCTGTGACGGAGTACAAACGCCTAGGGTGCTCAGAC
ThrProHisValLeuArgAlaThrAlaValThrGluTyrLysArgLeuGlyCysSerAsp

TCCGACATAATGAAGGTCACAGGACACGCAACCGCAAAGATGATATTTGCGTACGATAAA
SerAspIleMetLysValThrGlyHisAlaThrAlaLysMetIlePheAlaTyrAspLys

TCTTCTCGAGAAGACAACGCTTCAAAGAAGATGGCTCTAATATAGCCTAAAGGTGTTTTT
SerSerArgGluAspAsnAlaSerLysLysMetAlaLeuIleEnd

TCTGGCAACAGAATATGAATAT
```

FIG. 2

```
        3610                3630                3650
AAAATGGGAAATTCTGGTTTTTATTTGTATAACACTGAAAACTGCGTCTTTGCTGATAAT
ORF3>>MetGlyAsnSerGlyPheTyrLeuTyrAsnThrGluAsnCysValPheAlaAspAsn 3670                3690                3710
ATCAAAGTTGGGCAAATGACAGAGCCGCTCAAGGACCAGCAAATAATCCTTGGGACAACA
IleLysValGlyGlnMetThrGluProLeuLysAspGlnGlnIleIleLeuGlyThrThr 3730                3750                3770
TCAACACCTGTCGCAGCCAAAATGACAGCTTCTGATGGAATATCTTTAACAGTCTCCAAT
SerThrProValAlaAlaLysMetThrAlaSerAspGlyIleSerLeuThrValSerAsn 3790                3810                3830
AATTCATCAACCAATGCTTCTATTACAATTGGTTTGGATGCGGAAAAAGCTTACCAGCTT
AsnSerSerThrAsnAlaSerIleThrIleGlyLeuAspAlaGluLysAlaTyrGlnLeu 3850                3870                3890
ATTCTAGAAAAGTTGGGAGATCAAATTCTTGATGGAATTGCTGATACTATTGTTGATAGT
IleLeuGluLysLeuGlyAspGlnIleLeuAspGlyIleAlaAspThrIleValAspSer 3910                3930                3950
ACAGTCCAAGATATTTTAGACAAAATCAAAACAGACCCTTCTCTAGGTTTGTTGAAAGCT
ThrValGlnAspIleLeuAspLysIleLysThrAspProSerLeuGlyLeuLeuLysAla 3970                3990                4010
TTTAACAACTTTCCAATCACTAATAAAATTCAATGCAACGGGTTATTCACTCCCAGTAAC
PheAsnAsnPheProIleThrAsnLysIleGlnCysAsnGlyLeuPheThrProSerAsn 4030                4050                4070
ATTGAAACTTTATTAGGAGGAACTGAAATAGGAAAATTCACAGTCACACCCAAAAGCTCT
IleGluThrLeuLeuGlyGlyThrGluIleGlyLysPheThrValThrProLysSerSer 4090                4110                4130
GGGAGCATGTTCTTAGTCTCAGCAGATATTATTGCATCAAGAATGGAAGGCGGCGTTGTT
GlySerMetPheLeuValSerAlaAspIleIleAlaSerArgMetGluGlyGlyValVal 4150                4170                4190
CTAGCTTTGGTACGAGAAGGTGATTCTAAGCCCTGCGCGATTAGTTATGGATACTCATCA
LeuAlaLeuValArgGluGlyAspSerLysProCysAlaIleSerTyrGlyTyrSerSer 4210                4230                4250
GGCATTCCTAATTTATGTAGTCTAAGAACCAGTATTACTAATACAGGATTGACTCCGACA
GlyIleProAsnLeuCysSerLeuArgThrSerIleThrAsnThrGlyLeuThrProThr 4270                4290                4310
ACGTATTCATTACGTGTAGGCGGTTTAGAAAGCGGTGTGGTATGGGTTAATGCCCTTTCT
ThrTyrSerLeuArgValGlyGlyLeuGluSerGlyValValTrpValAsnAlaLeuSer 4330                4350                4370
AATGGCAATGATATTTTAGGAATAACAAATACTTCTAATGTATCTTTTTAGAGGTAATA
AsnGlyAsnAspIleLeuGlyIleThrAsnThrSerAsnValSerPheLeuGluValIle 4390                4410                4430
CCTCAAACAAACGCTTAAACAATTTTTATTGGATTTTTCTTATAGGTTTTATATTTAGAG
ProGlnThrAsnAlaEnd
```

FIG. 3

-106
MetSerLysThrThrLysLysPheAsnSerLeuCysIleAspLeuProArgAspLeuSer

LeuGluIleTyrGlnSerIleAlaSerValAlaThrGlySerGlyAspProHisSerAsp

AspPheThrAlaIleAlaTyrLeuArgAspGluLeuLeuThrLysHisProThrLeuGly

SerGlyAsnAspGluAlaThrArgArgThrLeuAlaIleAlaLysLeuArgGluAlaAsn

GlyAspArgGlyGlnIleAsnArgGluGlyPheLeuHisAspLysSerLeuSerTrpAsp
+1
IleArgAlaThrGlySerMetGlyAsnSerGlyPheTyrLeuTyrAsnThrGluAsnCys

ValPheAlaAspAsnIleLysValGlyGlnMetThrGluProLeuLysAspGlnGlnIle

IleLeuGlyThrThrSerThrProValAlaAlaLysMetThrAlaSerAspGlyIleSer

LeuThrValSerAsnAsnSerSerThrAsnAlaSerIleThrIleGlyLeuAspAlaGlu

LysAlaTyrGlnLeuIleLeuGluLysLeuGlyAspGlnIleLeuAspGlyIleAlaAsp

ThrIleValAspSerThrValGlnAspIleLeuAspLysIleLysThrAspProSerLeu

GlyLeuLeuLysAlaPheAsnAsnPheProIleThrAsnLysIleGlnCysAsnGlyLeu

PheThrProSerAsnIleGluThrLeuLeuGlyGlyThrGluIleGlyLysPheThrVal

ThrProLysSerSerGlySerMetPheLeuValSerAlaAspIleIleAlaSerArgMet

GluGlyGlyValValLeuAlaLeuValArgGluGlyAspSerLysProCysAlaIleSer

TyrGlyTyrSerSerGlyIleProAsnLeuCysSerLeuArgThrSerIleThrAsnThr

GlyLeuThrProThrThrTyrSerLeuArgValGlyGlyLeuGluSerGlyValValTrp

ValAsnAlaLeuSerAsnGlyAsnAspIleLeuGlyIleThrAsnThrSerAsnValSer

PheLeuGluValIleProGlnThrAsnAlaEnd

CHLAMYDIA TRACHOMATIS SEROTYPE D GENES

This application is a divisional of U.S. application Ser. No. 08/444,185, filed May 18, 1995, which is a continuation of U.S. application Ser. No. 08/180,528, filed Jan. 12, 1994, abandoned, which is a division of U.S. application Ser. No. 07/991,512, filed Dec. 17, 1992, abandoned, which is a continuation of U.S. application Ser. No. 07/661,820, filed Feb. 28, 1991, abandoned.

INVENTION FIELD

This invention refers to the PCTD plasmid isolated from *Chlamydia trachomatis* serotype D, cloned and sequenced and to the genes present in said plasmid, to the proteins expressed by said genes, to the expression vectors containing said genes and to the microrganisms transformed by said vectors. The invention further refers to the process for the preparation of genes and of said vectors and to the use of said proteins as antigens for the preparation of polyclonal and monoclonal antibodies apt to recognize *Chlamydia trachomatis* and hence useful for the preparation of vaccines capable of imparting a protective immunity against infections caused by *Chlamydia trachomatis* and pathologic conditions deriving from said infections and for the development of diagnostic methods for the search of specific antibodies produced following *C. trachomatis* infections.

PRIOR ART

Chlamydias are gram-negative bacteria, obligate intracellular parasites of eukariotic cells. Chlamydias show an extracellular infective and metabolically practically inert form, called elemental body (EB), and intracellular replicative forms called reticular bodies (RB).

The reticular bodies, after multiplication by binary fission, are transformed into elemental bodies which come out of the host cell and infect new cells.

The masses or mini-colonies of reticular and elemental bodies inside an infected cell constitute the characteristic "inclusions" visible at the optical microscope.

*Chlamydia trachomatis* (*C. trachomatis* or *CT*), a bacterial species pathogenic to man, is the etiological agent of venereal lymphogranuloma (VLG), of various inflammatory patologies of the genital male and female apparatus and of trachoma, a chronic disease which affects 500 million people and can lead to blindness. In the technical literature ca. 15 *CT* serotypes pathogenic to man were described and divided in two groups which differ both as to virulence and tissular tropism.

Twelve serotypes of the trachoma group (biovar) are identified as A to K and infect, in general, epithelial tissues, such as the ocular (trachoma) and uro-genital (cervicitis and urethritis) mucous membranes, and show a low virulence.

The venereal lymphogranuloma (VLG) serotypes ($L_1$, $L_2$ and $L_3$) cause instead an infection of the reticulo-endothelial tissue, mainly of the inguinal and femoral lymphonodi, and are highly invasive. Urethritis and cervicitis induced by *CT* (A to K serotypes) when not precociously diagnosed and treated by adequate therapy, may led to a variety of chronic inflammations, such as, e.g., vaginitis, salpingities and pelvic inflammation which may resolve in sterility and extrauterine pregnancy.

Furthermore the new born from infected mothers may contract pulmonary and/or ocular infections during delivery.

For said reason it is necessary to possess adequate diagnostic methods for determining *CT* and formulating effective vaccines against said bacterium.

As known, factors which determine the bacterial virulence are often encoded by genes present on plasmids.

In the literature, the presence is reported, in all 15 serotypes and in the clinical isolates examined up to now, of a plasmid of ca. 7.5 Kb referred to in the present invention as pCT followed by the denomination of the bacterial serotype concerned. For example: pCTD for the plasmid isolated from serotype D, etc.

Up to now, however, no specific function or products encoded by it were associated with said plasmid.

DETAILED DESCRIPTION OF THE INVENTION

A variant of the plasmid, corresponding to serotype D, was now isolated, indicated in what follows a pCTD, which comprises at least eight genes encoding for new proteins.

FIG. 1a shows the nucleotidic sequence of said plasmid and 7 of the 8 protein structures expressed by said sequence. The eighth protein structure, encoded on the DNA chain complemental to the one of FIG. 1a, is shown in FIG. 1b.

Object of the present invention are thus: the cloned and sequenced PCTD plasmid, the nucleotide sequences encoding for the above named proteins, the expression vectors containing one of said sequences or fragments thereof.

Further object of the present invention are the pCTD proteins or fragments of them having immunogenic properties.

Still another object of the present invention are the fusion polypeptides comprising one of said proteins or its fragments suitable as antigens.

The present invention further refers to the preparation of said proteins and of their fragments possessing immunogenic activity or of fused polypeptides comprising said proteins.

Said proteins, their fragments or fusion polypeptides comprising said proteins or their fragments, according to the invention may be employed to determine the *CT* produced infections in biological samples.

Said proteins, their fragments or fusion polypeptides comprising the protein or its fragments may further be employed, according to the invention, as antigens useful in the formulation of vaccines against infections due to *CT*.

According to the invention, said proteins, their fragments or fusion polypeptides may be used furthermore as antigens for the preparation of poly- or mono-clonal antibodies to be used in diagnostics.

In particular, the present invention relates to the pgp 3D protein encoded by the gene of the pCTD plasmid identified as ORF3D having the nucleotide sequence reported in FIG. 2, and characterized by a molecular weight of 27,802 and by the aminoacid sequence reported in FIG. 2.

According to the present invention, plasmid pCTD is obtained from the *C. trachomatis* G0/86 strain isolated from the urethra of a patient with non-gonococcic urethritis, and successively identified as serotype D by the immunofluorescence method described by Wang, S. P. and Grayston, J. T. [Am. J. Ophtalmol. 70; 367–374 (1970)].

The ORF3D gene may be isolated from the PCTD plasmid employing one of the known methods such as, e.g., the in vitro amplification method [Saiki, A. K. et al. Science, 239:487–491 (1988)] using as primers synthetic oligonucleotides having a primary structure suitably derived from the sequence data shown in FIGS. 1a and 1b. The thus emplified gene is then cloned in a vector placing it under the control of sequences regulating its expression.

One can similarly proceed for the other seven genes the nucleotide sequences of which are reported in FIGS. 1a and 1b.

The proteins encoded by said genes are represented by the aminoacid sequences also reported in FIGS. 1a and 1b.

Vectors suitable for the ends of the present invention may be plasmids with expression in host cells selected among the ones known and available commercially or at authorized collection centers. The cells transformed by said vectors are then cultivated in a suitable culture medium in the presence of carbon-, nitrogen- and mineral salts sources, possibly in induction conditions, at a temperature and time period selected in order to obtain the production of the desired protein.

Said protein, obtainable also as fused polypeptide, constituted by a polypeptide produced by the vector fused with the protein itself, is then separated and purified from the culture medium or from the cell lysate.

According to one embodiment of the present invention, the ORF3D gene is cloned in the plasmidic E. coli pEX34a vector, a derivative of pEX29 and pEX31 described by Strebel et al. [J.Virol., 57:983–991 (1986)], following the description by Nicosia et al. in Infect. Imm. 1987, Vol.55, 963–967.

The results show the presence in the bacterial extracts of a polypeptide, indicated as MS2-pgp3D, the sequence of which is shown in FIG. 3, with a mol. weight of ca. 39 Kd, consisting i.e. of a RNA-polymerase fragment of bacteriofage MS2, produced by the expression system of ca. 11 Kd and by the protein encoded by the ORF3D gene of ca. 28 Kd.

Said polypeptide employed as antigen in a Western-Blot assay, or in immunologic assays, is recognized by antibodies present in the serum of patients with CT infection and may further be employed for the production, in laboratory animals, of mono- and poly-clonal antibodies which recognize the – and react with the corresponding pgp3 protein, in all its variants, of C. trachomatis.

In accordance with the present invention the pCTD and p03/60/MCI plasmids were deposited as ATCC N° 68314 and ATCC N° 68315 respectively.

The experimental examples that follow are illustrative and non limitative of the invention.

EXAMPLE 1

Isolation of the pCTD Plasmid from C. trachomatis G0/86

C. trachomatis cells were isolated following known techniques from the urethra of a patient with non-genococcic urethritis. The strain, identified as serotype D by the micro-immunofluorescence technique described by Wang, S. P. and Grayston, J. T. [(1970), Am. J. Ophtalmol., 70: 367–374] is designated as G0/86.

The elemental bodies of said strain are then purified as described by Cevenini R. et al. [(1988), FEMS Microbiol. Letters, 56:41–46] on renografin$^R$ density discontinuous gradients (E.R. Squibb & Sons, Princeton, N.J.) according to what reported by Caldwell H. D. et al. [(1988) Infect. Immun. 31:1161–1176].

After purification, the elemental bodies (ca. 1.5 mg proteins) are lysated by incubation in 10 mM Tris-HC1, pH 8.0, 150 mM NaCl, 2 mM EDTA, 0.6% SDS and 100 mg/ml K Proteinase (Boehringer) at 37° C. for 3 hrs. The total nucleic acids are then extracted with phenol/chloroform, precipitated with ethanol, treated with pancreatic RNAse (250 ng/μl final concentration), further precipitated with ethanol and re-suspended in 800 μl water (365 ng/μl of DNA).

A 10 μl aliquot of said solution is then treated with 30 units (U) of BamHI restriction enzyme (Boehringer) at 37° C. for 2 hrs in 20 μl (final volume) of a digestion mixture suggested by the supplier. 3 μl of the resulting digestion mixture are ligated to 100 ng plasmidic pUC8 DNA previously digested with BamHI and dephosphorilated with calf gut phosphatase. The ligase reaction is effected overnight in 20 μl buffer containing 9 U T4 DNA ligase (Boehringer) at 18° C.

The ligation mixture is then employed to transform HB101 *E. coli* cells made competent by a treatment with $CaCl_2$ as described by Mandel and Higa [(1970) J. Mol. Biol: 53, 54]. The transformants are selected on LB agar Medium (DIFCO) with addition of 100 μg/ml ampicillin, at 37° C. overnight.

The positive clones (ampicillin resistant) (Amp$^R$) containing, that is, the recombinant pUC8 plasmid are transferred onto Hybond-N membranes (Amersham) and sorted by hybridization with three $^{32}$P marked oligonucleotides having the following nucleotidic sequences:

1) 5'ATGGGTAAAGGGATTTTATC3' (SEQ ID NO:1)

2) 5'CTATATTAGAGCCATCTTC3' (SEQ ID NO:2)

3) 5'TCAAAGCGCTTGCACGAAG3' (SEQ ID NO:3)

The above reported oligonucleotides are synthesized by means of an automatic synthesizer (Applied Biosystem Inc. Mod. 380A) following the methods and employing the reagents recommended by the manufacturers.

Four of the six plasmids isolated from the clones found positive at the hybridization, analyzed by electrophoresis on agarose 1% gel before and after digestion with BamHI are found to consist of the pUC8 plasmid nucleotidic sequence and of a nucleotidic insert of ca. 7.5 kilobases corresponding to the isolated *C.trachomatis G*0/86 plasmid.

The nucleotidic sequences of said insert is determined according to the method of Sanger F. [(1977) PNAS USA 74:5463–5467] utilizing a series of suitable primers. The sequencing reactions are performed on double helix DNA employing the Sequenase Kit (U.S. Biochemical Co. Cleveland, Ohio) as recommended by the firm.

The nucleotidic sequences of the ca. 7.5 kilobases plasmid named pCTD are reported in FIGS. 1*a* and 1*b*. The recombinant plasmid containing said insert is indicated as pUC8-pCTD.

EXAMPLE 2

Cloning of the DNA ORF3D Segment of Plasmid pCTD1D

The DNA fragment denoted as ORF3D(FIG. 2) of 792 bp is obtained through in vitro amplification according to the technique known as Polymerase Chain Reaction (PCR) described by Saiki A. K. et al. [(1988) Science 239:487–491].

The amplification is effected utilizing ca. 10 ng of the pUC8-pCTD plasmid and employing as primers two synthetic oligonucleotides (ORF31) and (ORF3dx) having respectively the following nucleotide sequences (SEQ ID NO:4 and SEQ ID NO:5):

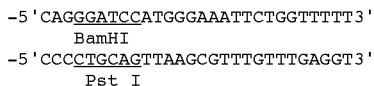
```
-5'CAGGGATCCATGGGAAATTCTGGTTTTT3'
        BamHI
-5'CCCCTGCAGTTAAGCGTTTGTTTGAGGT3'
       Pst I
```

Said oligonucleotides are complemental to ORF3 regions with the addition to the respective 5' terminals of a nucleotide sequence comprising the action site of a restriction enzyme selected among the ones present in the pEX34A vector (Strebel K. et al. [(1986, J. Virol.57: 983–991] utilized for the successive cloning. In particular, the site selected for ORF31 is the one for the BamHI enzyme, while for ORF3dx is the one of the PstI enzyme.

The amplification reaction is performed employing the reagents contained in the "Geneamp" Kit (Perkin Elmer-Cetus). 25 amplification cycles are effected. Each amplification cycle consists in heating the reaction mixture to 94° C. for one minute, to 50° C. for one minute and finally to 72° C. for one minute.

At the end of the amplification reaction the mixture is extracted, in succession, with an equal volume of phenol and of a chloroform-isoamyl alcohol mixture (24:1 v/v) and then submitted to forced dialysis by means of Centricon cartridges following the producer's (Amicon) instructions.

The DNA is then precipitated by adding to the obtained solution sodium acetate 3 M, pH 5.5 (1/10 of the volume) and cold (−20° C.) ethanol (3 vols.). The DNA precipitate is dissolved in 44 μl water. To the solution, 5 μl H buffer (Boehringer) and 1 μl PSTI restriction enzyme (20 units/μl) are added and the DNA is digested at 37° C. for 2 hours.

The digestion mixture is then extracted with phenol, chloroform/isoamyl alcohol and then the DNA is precipitated with ethanol (−20° C.). The precipitate, separated by centrifugation, is suspended again in 44 μl water and then digested with 20 U BamHI in 5 μl of B buffer (Boehringer) at 37° C. for 2 hours. The digestion mixture is extracted with phenol, chloroform/isoamyl alcohol and dialyzed by Centricon$^R$ cartridge.

At the same time, 10 μg of the pEX34A plasmidic vector are digested with the PstI and BamHI restriction enzymes as reported supra. The vector is dephosphorylated with alkaline phosphatase, extracted with phenol and chloroform/isoamyl alcohol, precipitated with ethanol (−20° C.) and re-suspended in 50 μl water.

1 μl (100 ng) of the vector and 2 μl (200 ng) of the amplified ORF3D segment are then ligated in 2 μl ligase buffer to which 2 μl ATP r, 1 μl T4 DNA ligase (9 units/μl) are added, adding water to a total volume of 20 μl. The ligase reaction is performed at 15° C. overnight. The ligase mixture is employed to transform 200 μl of a suspension of E. coli competent cells (K12-ΔH1-Δtrp) [Remaut E. et al. (1983), Gene 22:103–113]. After treatment at 30° C. for 5 minutes, to the cell suspension 800 μl LB medium are added, followed by incubation at 30° C. for 1 hour. Aliquots of the cell suspension (10 μl, 100 μl and 690 μl) are separately plated on plates of agarized (20 g/l) LB medium containing 100 μg/mg ampicillin and kept at 30° C. overnight.

The obtained clones (Amp$^R$) are transferred to a nitrocellulose membrane on a LB agar plate with added ampicillin, grown at 30° C. overnight, and then tested for hybridization with three oligonucleotidic probes (UB35, UB36, UB18) terminally marked with $^{32}$P having the following sequences:

I) 5'-ATGGGTAAAGGGATTTTATC3' (SEQ ID NO:1)
II) 5'-CTATATTAGAGCCATCTTC3' (SEQ ID NO:2)
III) 5'-TCAAAGCGCTTGCACGAAG3' (SEQ ID NO:3)

The hybridization test is performed according to known tecnique. From the colonies positive to hybridization the plasmids contained in them are prepared by minipreparation as described by Maniatis et al. (1982) and the ORF3D insert nucleotide sequence is controlled by known technique.

EXAMPLE 3

Expression of the MS2-gpg3 Recombination Protein

E. coli cells containing the pEX34 vector with the ORF3D insert are inoculated in duplicate in 10 ml LB medium with added 30 μg/ml ampicillin and cultivated at 30° C. overnight. The procedure described by Nicosia et al. [Inf. Imm. (1987) 55:963–967] is then followed, with the provision that one of two duplicates undergoes induction of the cloned gene by treatment at 42° C., while the other does not. Two protein extracts are thus obtained, produced by the bacterium, in 7M urea buffered at pH 8, one of which corresponds to the induced cells, and the other, as a control, to the non-induced cells. By analysis of the protein contents of both extracts by electrophoresis in SDS-polyacrylamide 15% gel according to known techniques, it is possible to deduct the presence of a protein species of 39,000 apparent mol.wt. which is present in a considerably greater amount in the induced extracts.

In the non-induced cell lysate no evidence of such a protein, but only the product of the vector alone, is found.

Said electrophoresis patterns may be analyzed by the Western Blot technique employing a monoclonal antibody (SCLAV0) specific for the 11 kd fragment generated by the pEX34 vector. In this way it is possible to demonstrate that the 39 kd band is a fusion protein containing said fragment.

EXAMPLE 4

Purification of MS2-pgp3 from E. coli K12Δ H1Δ trp Extracts

The protein extract, from induced bacterial cells, re-suspended in 7M urea, is dialyzed for 15 hrs. at 4° C. against a PBS buffer consisting of 0.4% KCl, 0.4% $KH_2PO_4$, 16% NaCl, 2.5% $NaH_2PO_4$.

During the dialysis a protein precipitate is obtained, which is separated by centrifuging and discarded. The surnatant is submitted to further purification by electrophoresis on preparative 12.5% acrylamide gels, and the protein band of 39,000 mol.wt. (MS2-pgp3D) is then extracted by electroelution from the gel.

The thus obtained MS2-pgp3 is precipitated by adding to the electroeluted solution 9 volumes of absolute acetone (−20° C.). The protein precipitate is separated by centrifuging, re-suspended in 90% acetone, centrifuged as above, precipitated in 96% acetone and centrifuged again. The precipitate is brought to dryness in a nitrogen stream and re-suspended in 200 μl sterile PBS at a final concentration of approximately 1.5 μg/pl.

The advantage of the effected dialysis is the elimination, with this procedure, of some E. coli proteins, in particular some with a molecular weight equal or very near to the one of the desired recombinant product, which may present a considerable hinderance in the electrophoretic and/or chromatographic purification.

EXAMPLE 5

Production of Polyclonal Anti-MS2-pGPG3 Antibodies

Utilizing the MS2-pgp3 protein, purified as in Example 4, 3 Balb/C 7–8 week old mice are immunized intraperitoneally. The immunization procedure comprises a first injection of 0.2 ml/mouse of an emulsion consisting of one part by vol. of the purified protein solution (1.5 µg/uml) and five parts of Freund complete adjuvant (FCA).

The thus inoculated protein amount is thus ca. 50 µg/mouse.

After 1 week the mice are immunized with the said same emulsion, followed by a 800 µl Pristane injection. After 1 week from the second inoculation, the mice are intraperitoneally immunized with 0.2 ml of a solution similar to the first one. Finally, after two weeks from the third inoculation a booster immunization is effected.

The thus induced antibodies are collected in the ascitic fluid formed after the above described treatment.

The anti MS2-pgp3 antibody titres show values comprised between 1:8000 and 1:10.000 evaluated by analysis with Western Blot containing the MS2-pgp3 protein.

The reactivity of said antibodies to the native antigen (pgp3) was evaluated according to the following methods:

analysis with Western Blot containing total protein extracts of elemental purified CT bodies;

immunofluorescence on McCoy cells cultures infected with CT.

The results of the above tests show that the anti MS2-pgp3 antibodies are able to reveal *C. trachomatis* inclusions in infected cells (see immunofluorescence test) and recognize a protein present in the bacterium protein extracts and having a mol.wt. of 28 kd, equivalent, that is, to the one of the protein encoded by ORF3D (see Western Blot test).

EXAMPLE 6

To the end of preparing monoclonal anti-MS2-pgp3 antibodies, the mice, immunized as above described, are sacrificed, the spleens extracted and utilized for the preparation of hybridomas operating according to the technique described by Davis L. G. [Basic methods in molecular biology—Elsevier Edit., New York (1986)]. The screening of the thus obtained hybridomas is performed as described for the polyclonal antibodies. In particular, a screening was performed with induced *E. coli* extracts (see Example 3) containing the MS2-pgp3 protein or the polypeptide encoded by the pEX34 vector alone; obviously, the clones were selected which produced antibodies reacting only with the recombinant product. With such pgp3-specific antibodies, results are obtained which are superimposable to the ones obtained with the above described polyclonal antibodies.

EXAMPLE 7

Serum samples from 20 patients with Chlamydia generated infections were collected. Said sera contained anti-Chlamydia antibodies with titres comprised between 128 and 512, as determined by immunofluorescence against single antigen (LGV2). 15 control sera not containing anti-Chlamydia antibodies were obtained from healty donors. Western Blots were prepared, as above described, containing the MS2-pgp3 protein. These were incubated with the sera under examination diluted 1:100 and successively with peroxidase marked rabbit (anti human IgG) immunoglobines. 16 of the 20 infected patients sera contained antibodies apt to react with MS2-pgp3. The 15 healthy control sera did not give any reaction with said protein.

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ATGGGTAAAG GGATTTTATC                                20

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CTATATTAGA GCCATCTTC                                19

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TCAAAGCGCT TGCACGAAG                                                    19

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CAGGGATCCA TGGGAAATTC TGGTTTTT                                          28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCCCTGCAGT TAAGCGTTTG TTTGAGGT                                          28

(2) INFORMATION FOR SEQ ID NO:6:

(i) SEQUENCE CHARACTERISTICS:
        (A) LENGTH: 7502 base pairs
        (B) TYPE: nucleic acid
        (C) STRANDEDNESS: double
        (D) TOPOLOGY: circular (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(xi) SEQUENCE DESCRIPTION: SEQ ID NO:6:

ATATTCATAT TCTGTTGCCA GAAAAAACAC CTTTAGGCTA TATTAGAGCC ATCTTCTTTG        60

AAGCGTTGTC TTCTCGAGAA GATTTATCGT ACGCAAATAT CATCTTTGCG GTTGCGTGTC       120

CTGTGACCTT CATTATGTCG GAGTCTGAGC ACCCTAGGCG TTTGTACTCC GTCACAGCGG       180

TTGCTCGAAG CACGTGCGGG GTTATTTTAA AAGGGATTGC AGCTTGTAGT CCTGCTTGAG       240

AGAACGTGCG GGCGATTTGC CTTAACCCCA CCATTTTTCC GGAGCGAGTT ACGAAGACAA       300

AACCTCTTCG TTGACCGATG TACTCTTGTA GAAAGTGCAT AAACTTCTGA GGATAAGTTA       360

TAATAATCCT CTTTTCTGTC TGACGGTTCT TAAGCTGGGA GAAAGAAATG GTAGCTTGTT       420

GGAAACAAAT CTGACTAATC TCCAAGCTTA AGACTTCAGA GGAGCGTTTA CCTCCTTGGA       480

GCATTGTCTG GGCGATCAAC CAATCCCGGG CATTGATTTT TTTTAGCTCT TTTAGGAAGG       540

-continued

```
ATGCTGTTTG CAAACTGTTC ATCGCATCCG TTTTTACTAT TTCCCTGGTT TTAAAAAATG    600
TTCGACTATT TTCTTGTTTA GAAGGTTGCG CTATAGCGAC TATTCCTTGA GTCATCCTGT    660
TTAGGAATCT TGTTAAGGAA ATATAGCTTG CTGCTCGAAC TTGTTTAGTA CCTTCGGTCC    720
AAGAAGTCTT GGCAGAGGAA ACTTTTTTAA TCGCATCTAG GATTAGATTA TGATTTAAAA    780
GGGAAAACTC TTGCAGATTC ATATCCAAGG ACAATAGACC AATCTTTTCT AAAGACAAAA    840
AAGATCCTCG ATATGATCTA CAAGTATGTT TGTTGAGTGA TGCGGTCCAA TGCATAATAA    900
CTTCGAATAA GGAGAAGCTT TTCATGCGTT TCCAATAGGA TTCTTGGCGA ATTTTTAAAA    960
CTTCCTGATA AGACTTTTCA CTATATTCTA ACGACATTTC TTGCTGCAAA GATAAAATCC   1020
CTTTACCCAT GAAATCCCTC GTGATATAAC CTATCCGTAA AATGTCCTGA TTAGTGAAAT   1080
AATCAGGTTG TTAACAGGAT AGCACGCTCG GTATTTTTTT ATATAAACAT GAAAACTCGT   1140
TCCGAAATAG AAAATCGCAT GCAAGATATC GAGTATGCGT TGTTAGGTAA AGCTCTGATA   1200
TTTGAAGACT CTACTGAGTA TATTCTGAGG CAGCTTGCTA ATTATGAGTT TAAGTGTTCT   1260
CATCATAAAA ACATATTCAT AGTATTTAAA CACTTAAAAG ACAATGGATT ACCTATAACT   1320
GTAGACTCGG CTTGGGAAGA GCTTTTGCGG CGTCGTATCA AGATATGGA CAAATCGTAT    1380
CTCGGGTTAA TGTTGCATGA TGCTTTATCA AATGACAAGC TTAGATCCGT TTCTCATACG   1440
GTTTTCCTCG ATGATTTGAG CGTGTGTAGC GCTGAAGAAA ATTTGAGTAA TTTCATTTTC   1500
CGCTCGTTTA ATGAGTACAA TGAAAATCCA TTGCGTAGAT CTCCGTTTCT ATTGCTTGAG   1560
CGTATAAAGG GAAGGCTTGA TAGTGCTATA GCAAAGACTT TTTCTATTCG CAGCGCTAGA   1620
GGCCGGTCTA TTTATGATAT ATTCTCACAG TCAGAAATTG GAGTGCTGGC TCGTATAAAA   1680
AAAAGACGAG TAGCGTTCTC TGAGAATCAA AATTCTTTCT TTGATGGCTT CCCAACAGGA   1740
TACAAGGATA TTGATGATAA AGGAGTTATC TTAGCTAAAG GTAATTTCGT GATTATAGCA   1800
GCTAGACCAT CTATAGGGAA AACAGCTTTA GCTATAGACA TGGCGATAAA TCTTGCGGTT   1860
ACTCAACAGC GTAGAGTTGG TTTCCTATCT CTAGAAATGA GCGCAGGTCA AATTGTTGAG   1920
CGGATTATTG CTAATTTAAC AGGAATATCT GGTGAAAAAT TACAAAGAGG GGATCTCTCT   1980
AAAGAAGAAT TATTCCGAGT AGAAGAAGCT GGAGAAACGG TTAGAGAATC ACATTTTTAT   2040
ATCTGCAGTG ATAGTCAGTA TAAGCTTAAC TTAATCGCGA ATCAGATCCG GTTGCTGAGA   2100
AAAGAAGATC GAGTAGACGT AATATTTATC GATTACTTGC AGTTGATCAA CTCATCGGTT   2160
GGAGAAAATC GTCAAAATGA AATAGCAGAT ATATCTAGAA CCTTAAGAGG TTTAGCCTCA   2220
GAGCTAAACA TTCCTATAGT TTGTTTATCC CAACTATCTA GAAAAGTTGA GGATAGAGCA   2280
AATAAAGTTC CCATGCTTTC AGATTTGCGA GACAGCGGTC AAATAGAGCA AGACGCAGAT   2340
GTGATTTTGT TTATCAATAG GAAGGAATCG TCTTCTAATT GTGAGATAAC TGTTGGGAAA   2400
AATAGACATG GATCGGTTTT CTCTTCGGTA TTACATTTCG ATCCAAAAAT TAGTAAATTC   2460
TCCGCTATTA AAAAGTATG GTAAATTATA GTAACTGCCA CTTCATCAAA AGTCCTATCC    2520
ACCTTGAAAA TCGAAGTTT GGAAGAAGAC CTGGTCAATC TATTAAGATA TCTCCCAAAT    2580
TGGCTCAAAA TGGGATGGTA GAAGTTATAG GTCTTGATTT TCTTTCATCT CATTACCATG   2640
CATTAGCAGC TATCCAAAGA TTACTGACCG CAACGAATTA CAAGGGGAAC ACAAAAGGGG   2700
TTGTTTTATC CAGAGAATCA AATAGTTTTC AATTTGAAGG ATGGATACCA AGAATCCGTT   2760
TTACAAAAAC TGAATTCTTA GAGGCTTATG GAGTTAAGCG GTATAAAACA TCCAGAAATA   2820
AGTATGAGTT TAGTGGAAAA GAAGCTGAAA CTGCTTTAGA AGCCTTATAC CATTTAGGAC   2880
```

-continued

```
ATCAACCGTT TTTAATAGTG GCAACTAGAA CTCGATGGAC TAATGAACA  CAAATAGTAG    2940

ACCGTTACCA AACTCTTTCT CCGATCATTA GGATTTACGA AGGATGGGAA GGTTTAACTG    3000

ACGAAGAAAA TATAGATATA GACTTAACAC CTTTTAATTC ACCACCTACA CGGAAACATA    3060

AAGGGTTCGT TGTAGAGCCA TGTCCTATCT TGGTAGATCA AATAGAATCC TACTTTGTAA    3120

TCAAGCCTGC AAATGTATAC CAAGAAATAA AAATGCGTTT CCCAAATGCA TCAAAGTATG    3180

CTTACACATT TATCGACTGG GTGATTACAG CAGCTGCGAA AAAGAGACGA AAATTAACTA    3240

AGGATAATTC TTGGCCAGAA AACTTGTTAT TAAACGTTAA CGTTAAAAGT CTTGCATATA    3300

TTTTAAGGAT GAATCGGTAC ATCTGTACAA GGAACTGGAA AAAAATCGAG TTAGCTATCG    3360

ATAAATGTAT AGAAATCGCC ATTCAGCTTG GCTGGTTATC TAGAAGAAAA CGCATTGAAT    3420

TTCTGGATTC TTCTAAACTC TCTAAAAAAG AAATTCTATA TCTAAATAAA GAGCGCTTTG    3480

AAGAAATAAC TAAGAAATCT AAAGAACAAA TGGAACAATT AGAACAAGAA TCTATTAATT    3540

AATAGCAAGC TTGAAACTAA AAACCTAATT TATTTAAAGC TCAAAATAAA AAAGAGTTTT    3600

AAAATGGGAA ATTCTGGTTT TTATTTGTAT AACACTGAAA ACTGCGTCTT TGCTGATAAT    3660

ATCAAAGTTG GGCAAATGAC AGAGCCGCTC AAGGACCAGC AAATAATCCT TGGGACAACA    3720

TCAACACCTG TCGCAGCCAA AATGACAGCT TCTGATGGAA TATCTTTAAC AGTCTCCAAT    3780

AATTCATCAA CCAATGCTTC TATTACAATT GGTTTGGATG CGGAAAAAGC TTACCAGCTT    3840

ATTCTAGAAA AGTTGGGAGA TCAAATTCTT GATGGAATTG CTGATACTAT TGTTGATAGT    3900

ACAGTCCAAG ATATTTTAGA CAAAATCAAA ACAGACCCTT CTCTAGGTTT GTTGAAAGCT    3960

TTTAACAACT TTCCAATCAC TAATAAAATT CAATGCAACG GGTTATTCAC TCCCAGTAAC    4020

ATTGAAACTT TATTAGGAGG AACTGAAATA GGAAAATTCA CAGTCACACC CAAAAGCTCT    4080

GGGAGCATGT TCTTAGTCTC AGCAGATATT ATTGCATCAA GAATGGAAGG CGGCGTTGTT    4140

CTAGCTTTGG TACGAGAAGG TGATTCTAAG CCCTGCGCGA TTAGTTATGG ATACTCATCA    4200

GGCATTCCTA ATTTATGTAG TCTAAGAACC AGTATTACTA ATACAGGATT GACTCCGACA    4260

ACGTATTCAT TACGTGTAGG CGGTTTAGAA AGCGGTGTGG TATGGGTTAA TGCCCTTTCT    4320

AATGGCAATG ATATTTTAGG AATAACAAAT ACTTCTAATG TATCTTTTTT AGAGGTAATA    4380

CCTCAAACAA ACGCTTAAAC AATTTTTATT GGATTTTTCT TATAGGTTTT ATATTTAGAG    4440

AAAACAGTTC GAATTACGGG GTTTGTTATG CAAAATAAAA GAAAAGTGAG GGACGATTTT    4500

ATTAAAATTG TTAAAGATGT GAAAAAAGAT TTCCCCGAAT TAGACCTAAA AATACGAGTA    4560

AACAAGGAAA AAGTAACTTT CTTAAATTCT CCCTTAGAAC TCTACCATAA AAGTGTCTCA    4620

CTAATTCTAG GACTGCTTCA ACAAATAGAA AACTCTTTAG GATTATTCCC AGACTCTCCT    4680

GTTCTTGAAA AATTAGAGGA TAACAGTTTA AAGCTAAAAA AGGCTTTGAT TATGCTTATC    4740

TTGTCTAGAA AAGACATGTT TTCCAAGGCT GAATAGACAA CTTACTCTAA CGTTGGAGTT    4800

GATTTGCACA CCTTAGTTTT TTGCTCTTTT AAGGGAGGAA CTGGAAAAAC AACACTTTCT    4860

CTAAACGTGG GATGCAACTT GGCCCAATTT TTAGGGAAAA AAGTGTTACT TGCTGACCTA    4920

GACCCGCAAT CCAATTTATC TTCTGGATTG GGGGCTAGTG TCAGAAGTGA CCAAAAAGGC    4980

TTGCACGACA TAGTATACAC ATCAAACGAT TTAAAATCAA TCATTTGCGA AACAAAAAAA    5040

GATAGTGTGG ACCTAATTCC TGCATCATTT TCATCCGAAC AGTTTAGAGA ATTGGATATT    5100

CATAGAGGAC CTAGTAACAA CTTAAAGTTA TTTCTGAATG AGTACTGCGC TCCTTTTTAT    5160

GACATCTGCA TAATAGACAC TCCACCTAGC CTAGGAGGGT TAACGAAAGA AGCTTTTGTT    5220

GCAGGAGACA AATTAATTGC TTGTTTAACT CCAGAACCTT TTTCTATTCT AGGGTTACAA    5280
```

-continued

```
AAGATACGTG AATTCTTAAG TTCGGTCGGA AAACCTGAAG AAGAACACAT TCTTGGAATA    5340

GCTTTGTCTT TTTGGGATGA TCGTAACTCG ACTAACCAAA TGTATATAGA CATTATCGAG    5400

TCTATTTACA AAAACAAGCT TTTTTCAACA AAAATTCGTC GAGATATTTC TCTCAGCCGT    5460

TCTCTTCTTA AAGAAGATTC TGTAGCTAAT GTCTATCCAA ATTCTAGGGC CGCAGAAGAT    5520

ATTCTGAAGT TAACGCATGA AATAGCAAAT ATTTTGCATA TCGAATATGA ACGAGATTAC    5580

TCTCAGAGGA CAACGTGAAC AAACTAAAAA AGAAGCGGA TGTCTTTTTT AAAAAAAATC     5640

AAACTGCCGC TTCTCTAGAT TTTAAGAAGA CGCTTCCCTC CATTGAACTA TTCTCAGCAA    5700

CTTTGAATTC TGAGGAAAGT CAGAGTTTGG ATCGATTATT TTTATCAGAG TCCCAAAACT    5760

ATTCGGATGA AGAATTTTAT CAAGAAGACA TCCTAGCGGT AAAACTGCTT ACTGGTCAGA    5820

TAAAATCCAT ACAGAAGCAA CACGTACTTC TTTTAGGAGA AAAAATCTAT AATGCTAGAA    5880

AAATCCTGAG TAAGGATCAC TTCTCCTCAA CAACTTTTTC ATCTTGGATA GAGTTAGTTT    5940

TTAGAACTAA GTCTTCTGCT TACAATGCTC TTGCATATTA CGAGCTTTTT ATAAACCTCC    6000

CCAACCAAAC TCTACAAAAA GAGTTTCAAT CGATCCCCTA TAAATCCGCA TATATTTTGG    6060

CCGCTAGAAA AGGCGATTTA AAAACCAAGG TCGATGTGAT AGGGAAAGTA TGTGGAATGT    6120

CGAACTCATC GGCGATAAGG GTGTTGGATC AATTTCTTCC TTCATCTAGA AACAAAGACG    6180

TTAGAGAAAC GATAGATAAG TCTGATTCAG AGAAGAATCG CCAATTATCT GATTTCTTAA    6240

TAGAGATACT TCGCATCATG TGTTCCGGAG TTTCTTTGTC CTCCTATAAC GAAAATCTTC    6300

TACAACAGCT TTTTGAACTT TTTAAGCAAA AGAGCTGATC CTCCGTCAGC TCATATATAT    6360

ATATCTATTA TATATATATA TTTAGGGATT TGATTTCACG AGAGAGATTT GCAACTCTTG    6420

GTGGTAGACT TTGCAACTCT TGGTGGTAGA CTTTGCAACT CTTGGTGGTA GACTTTGCAA    6480

CTCTTGGTGG TAGACTTGGT CATAATGGAC TTTTGTTAAA AAATTATTA AAATCTTAGA     6540

GCTCCGATTT TGAATAGCTT TGGTTAAGAA AATGGGCTCG ATGGCTTTCC ATAAAAGTAG    6600

ATTGTTTTTA ACTTTTGGGG ACGCGTCGGA AATTTGGTTA TCTACTTTAT CTTATCTAAC    6660

TAGAAAAAAT TATGCGTCTG GGATTAACTT TCTTGTTTCT TTAGAGATTC TGGATTTATC    6720

GGAAACCTTG ATAAAGGCTA TTTCTCTTGA CCACAGCGAA TCTTTGTTTA AAATCAAGTC    6780

TCTAGATGTT TTTAATGGAA AAGTTGTTTC AGAGGCATCT AAACAGGCTA GAGCGGCATG    6840

CTACATATCT TTCACAAAGT TTTTGTATAG ATTGACCAAG GGATATATTA AACCCGCTAT    6900

TCCATTGAAA GATTTTGGAA ACACTACATT TTTTAAAATC CGAGACAAAA TCAAAACAGA    6960

ATCGATTTCT AAGCAGGAAT GGACAGTTTT TTTTGAAGCG CTCCGGATAG TGAATTATAG    7020

AGACTATTTA ATCGGTAAAT TGATTGTACA AGGGATCCGT AAGTTAGACG AAATTTTGTC    7080

TTTGCGCACA GACGATCTAT TTTTTGCATC CAATCAGATT TCCTTTCGCA TTAAAAAAAG    7140

ACAGAATAAA GAAACCAAAA TTCTAATCAC ATTTCCTATC AGCTTAATGG AAGAGTTGCA    7200

AAAATACACT TGTGGGAGAA ATGGGAGAGT ATTTGTTTCT AAAATAGGGA TTCCTGTAAC    7260

AACAAGTCAG GTTGCGCATA ATTTTAGGCT TGCAGAGTTC CATAGTGCTA TGAAAATAAA    7320

AATTACTCCC AGAGTACTTC GTGCAAGCGC TTTGATTCAT TTAAAGCAAA TAGGATTAAA    7380

AGATGAGGAA ATCATGCGTA TTTCCTGTCT TTCATCGAGA CAAAGTGTGT GTTCTTATTG    7440

TTCTGGGGAA GAGGTAATTC CTCTAGTACA AACACCCACA ATATTGTGAT ATAATTAAAA    7500

TT                                                                  7502
```

(2) INFORMATION FOR SEQ ID NO:7:

```
    (i) SEQUENCE CHARACTERISTICS:
        (A) LENGTH: 1356 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D

```
Ala Arg Pro Ser Ile Gly Lys Thr Ala Leu Ala Ile Asp Met Ala Ile
225                 230                 235                 240

AAT CTT GCG GTT ACT CAA CAG CGT AGA GTT GGT TTC CTA TCT CTA GAA      768
Asn Leu Ala Val Thr Gln Gln Arg Arg Val Gly Phe Leu Ser Leu Glu
                245                 250                 255

ATG AGC GCA GGT CAA ATT GTT GAG CGG ATT ATT GCT AAT TTA ACA GGA      816
Met Ser Ala Gly Gln Ile Val Glu Arg Ile Ile Ala Asn Leu Thr Gly
                260                 265                 270

ATA TCT GGT GAA AAA TTA CAA AGA GGG GAT CTC TCT AAA GAA GAA TTA      864
Ile Ser Gly Glu Lys Leu Gln Arg Gly Asp Leu Ser Lys Glu Glu Leu
            275                 280                 285

TTC CGA GTA GAA GAA GCT GGA GAA ACG GTT AGA GAA TCA CAT TTT TAT      912
Phe Arg Val Glu Glu Ala Gly Glu Thr Val Arg Glu Ser His Phe Tyr
        290                 295                 300

ATC TGC AGT GAT AGT CAG TAT AAG CTT AAC TTA ATC GCG AAT CAG ATC      960
Ile Cys Ser Asp Ser Gln Tyr Lys Leu Asn Leu Ile Ala Asn Gln Ile
305                 310                 315                 320

CGG TTG CTG AGA AAA GAA GAT CGA GTA GAC GTA ATA TTT ATC GAT TAC     1008
Arg Leu Leu Arg Lys Glu Asp Arg Val Asp Val Ile Phe Ile Asp Tyr
                325                 330                 335

TTG CAG TTG ATC AAC TCA TCG GTT GGA GAA AAT CGT CAA AAT GAA ATA     1056
Leu Gln Leu Ile Asn Ser Ser Val Gly Glu Asn Arg Gln Asn Glu Ile
                340                 345                 350

GCA GAT ATA TCT AGA ACC TTA AGA GGT TTA GCC TCA GAG CTA AAC ATT     1104
Ala Asp Ile Ser Arg Thr Leu Arg Gly Leu Ala Ser Glu Leu Asn Ile
            355                 360                 365

CCT ATA GTT TGT TTA TCC CAA CTA TCT AGA AAA GTT GAG GAT AGA GCA     1152
Pro Ile Val Cys Leu Ser Gln Leu Ser Arg Lys Val Glu Asp Arg Ala
370                 375                 380

AAT AAA GTT CCC ATG CTT TCA GAT TTG CGA GAC AGC GGT CAA ATA GAG     1200
Asn Lys Val Pro Met Leu Ser Asp Leu Arg Asp Ser Gly Gln Ile Glu
385                 390                 395                 400

CAA GAC GCA GAT GTG ATT TTG TTT ATC AAT AGG AAG GAA TCG TCT TCT     1248
Gln Asp Ala Asp Val Ile Leu Phe Ile Asn Arg Lys Glu Ser Ser Ser
                405                 410                 415

AAT TGT GAG ATA ACT GTT GGG AAA AAT AGA CAT GGA TCG GTT TTC TCT     1296
Asn Cys Glu Ile Thr Val Gly Lys Asn Arg His Gly Ser Val Phe Ser
            420                 425                 430

TCG GTA TTA CAT TTC GAT CCA AAA ATT AGT AAA TTC TCC GCT ATT AAA     1344
Ser Val Leu His Phe Asp Pro Lys Ile Ser Lys Phe Ser Ala Ile Lys
        435                 440                 445

AAA GTA TGG TAA                                                      1356
Lys Val Trp
    450

(2) INFORMATION FOR SEQ ID NO:8:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:8:

Met Lys Thr Arg Ser Glu Ile Glu Asn Arg Met Gln Asp Ile Glu Tyr
1               5                   10                  15

Ala Leu Leu Gly Lys Ala Leu Ile Phe Glu Asp Ser Thr Glu Tyr Ile
            20                  25                  30

Leu Arg Gln Leu Ala Asn Tyr Glu Phe Lys Cys Ser His His Lys Asn
        35                  40                  45
```

```
Ile Phe Ile Val Phe Lys His Leu Lys Asp Asn Gly Leu Pro Ile Thr
    50                  55                  60
Val Asp Ser Ala Trp Glu Leu Leu Arg Arg Arg Ile Lys Asp Met
 65                  70                  75                  80
Asp Lys Ser Tyr Leu Gly Leu Met Leu His Asp Ala Leu Ser Asn Asp
                85                  90                  95
Lys Leu Arg Ser Val Ser His Thr Val Phe Leu Asp Asp Leu Ser Val
                100                 105                 110
Cys Ser Ala Glu Glu Asn Leu Ser Asn Phe Ile Phe Arg Ser Phe Asn
                115                 120                 125
Glu Tyr Asn Glu Asn Pro Leu Arg Arg Ser Pro Phe Leu Leu Leu Glu
            130                 135                 140
Arg Ile Lys Gly Arg Leu Asp Ser Ala Ile Ala Lys Thr Phe Ser Ile
145                 150                 155                 160
Arg Ser Ala Arg Gly Arg Ser Ile Tyr Asp Ile Phe Ser Gln Ser Glu
                165                 170                 175
Ile Gly Val Leu Ala Arg Ile Lys Lys Arg Arg Val Ala Phe Ser Glu
                180                 185                 190
Asn Gln Asn Ser Phe Phe Asp Gly Phe Pro Thr Gly Tyr Lys Asp Ile
            195                 200                 205
Asp Asp Lys Gly Val Ile Leu Ala Lys Gly Asn Phe Val Ile Ile Ala
210                 215                 220
Ala Arg Pro Ser Ile Gly Lys Thr Ala Leu Ala Ile Asp Met Ala Ile
225                 230                 235                 240
Asn Leu Ala Val Thr Gln Gln Arg Arg Val Gly Phe Leu Ser Leu Glu
                245                 250                 255
Met Ser Ala Gly Gln Ile Val Glu Arg Ile Ile Ala Asn Leu Thr Gly
                260                 265                 270
Ile Ser Gly Glu Lys Leu Gln Arg Gly Asp Leu Ser Lys Glu Glu Leu
            275                 280                 285
Phe Arg Val Glu Glu Ala Gly Glu Thr Val Arg Glu Ser His Phe Tyr
            290                 295                 300
Ile Cys Ser Asp Ser Gln Tyr Lys Leu Asn Leu Ile Ala Asn Gln Ile
305                 310                 315                 320
Arg Leu Leu Arg Lys Glu Asp Arg Val Asp Val Ile Phe Ile Asp Tyr
                325                 330                 335
Leu Gln Leu Ile Asn Ser Ser Val Gly Glu Asn Arg Gln Asn Glu Ile
            340                 345                 350
Ala Asp Ile Ser Arg Thr Leu Arg Gly Leu Ala Ser Glu Leu Asn Ile
            355                 360                 365
Pro Ile Val Cys Leu Ser Gln Leu Ser Arg Lys Val Glu Asp Arg Ala
370                 375                 380
Asn Lys Val Pro Met Leu Ser Asp Leu Arg Asp Ser Gly Gln Ile Glu
385                 390                 395                 400
Gln Asp Ala Asp Val Ile Leu Phe Ile Asn Arg Lys Glu Ser Ser Ser
                405                 410                 415
Asn Cys Glu Ile Thr Val Gly Lys Asn Arg His Gly Ser Val Phe Ser
            420                 425                 430
Ser Val Leu His Phe Asp Pro Lys Ile Ser Lys Phe Ser Ala Ile Lys
            435                 440                 445
Lys Val Trp
        450
```

(2) INFORMATION FOR SEQ ID NO:9:

(i) SEQUENCE CHARACTERISTICS:
        (A) LENGTH: 1065 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..1062

(xi) SEQUENCE DESCRIPTION: SEQ ID NO:9:

```
ATG GTA AAT TAT AGT AAC TGC CAC TTC ATC AAA AGT CCT ATC CAC CTT       48
Met Val Asn Tyr Ser Asn Cys His Phe Ile Lys Ser Pro Ile His Leu
  1               5                  10                  15

GAA AAT CAG AAG TTT GGA AGA AGA CCT GGT CAA TCT ATT AAG ATA TCT       96
Glu Asn Gln Lys Phe Gly Arg Arg Pro Gly Gln Ser Ile Lys Ile Ser
                 20                  25                  30

CCC AAA TTG GCT CAA AAT GGG ATG GTA GAA GTT ATA GGT CTT GAT TTT      144
Pro Lys Leu Ala Gln Asn Gly Met Val Glu Val Ile Gly Leu Asp Phe
             35                  40                  45

CTT TCA TCT CAT TAC CAT GCA TTA GCA GCT ATC CAA AGA TTA CTG ACC      192
Leu Ser Ser His Tyr His Ala Leu Ala Ala Ile Gln Arg Leu Leu Thr
         50                  55                  60

GCA ACG AAT TAC AAG GGG AAC ACA AAA GGG GTT GTT TTA TCC AGA GAA      240
Ala Thr Asn Tyr Lys Gly Asn Thr Lys Gly Val Val Leu Ser Arg Glu
 65                  70                  75                  80

TCA AAT AGT TTT CAA TTT GAA GGA TGG ATA CCA AGA ATC CGT TTT ACA      288
Ser Asn Ser Phe Gln Phe Glu Gly Trp Ile Pro Arg Ile Arg Phe Thr
                 85                  90                  95

AAA ACT GAA TTC TTA GAG GCT TAT GGA GTT AAG CGG TAT AAA ACA TCC      336
Lys Thr Glu Phe Leu Glu Ala Tyr Gly Val Lys Arg Tyr Lys Thr Ser
                100                 105                 110

AGA AAT AAG TAT GAG TTT AGT GGA AAA GAA GCT GAA ACT GCT TTA GAA      384
Arg Asn Lys Tyr Glu Phe Ser Gly Lys Glu Ala Glu Thr Ala Leu Glu
            115                 120                 125

GCC TTA TAC CAT TTA GGA CAT CAA CCG TTT TTA ATA GTG GCA ACT AGA      432
Ala Leu Tyr His Leu Gly His Gln Pro Phe Leu Ile Val Ala Thr Arg
        130                 135                 140

ACT CGA TGG ACT AAT GGA ACA CAA ATA GTA GAC CGT TAC CAA ACT CTT      480
Thr Arg Trp Thr Asn Gly Thr Gln Ile Val Asp Arg Tyr Gln Thr Leu
145                 150                 155                 160

TCT CCG ATC ATT AGG ATT TAC GAA GGA TGG GAA GGT TTA ACT GAC GAA      528
Ser Pro Ile Ile Arg Ile Tyr Glu Gly Trp Glu Gly Leu Thr Asp Glu
                165                 170                 175

GAA AAT ATA GAT ATA GAC TTA ACA CCT TTT AAT TCA CCA CCT ACA CGG      576
Glu Asn Ile Asp Ile Asp Leu Thr Pro Phe Asn Ser Pro Pro Thr Arg
            180                 185                 190

AAA CAT AAA GGG TTC GTT GTA GAG CCA TGT CCT ATC TTG GTA GAT CAA      624
Lys His Lys Gly Phe Val Val Glu Pro Cys Pro Ile Leu Val Asp Gln
        195                 200                 205

ATA GAA TCC TAC TTT GTA ATC AAG CCT GCA AAT GTA TAC CAA GAA ATA      672
Ile Glu Ser Tyr Phe Val Ile Lys Pro Ala Asn Val Tyr Gln Glu Ile
        210                 215                 220
```

```
AAA ATG CGT TTC CCA AAT GCA TCA AAG TAT GCT TAC ACA TTT ATC GAC      720
Lys Met Arg Phe Pro Asn Ala Ser Lys Tyr Ala Tyr Thr Phe Ile Asp
225             230                 235                 240

TGG GTG ATT ACA GCA GCT GCG AAA AAG AGA CGA AAA TTA ACT AAG GAT      768
Trp Val Ile Thr Ala Ala Ala Lys Lys Arg Arg Lys Leu Thr Lys Asp
                245                 250                 255

AAT TCT TGG CCA GAA AAC TTG TTA TTA AAC GTT AAC GTT AAA AGT CTT      816
Asn Ser Trp Pro Glu Asn Leu Leu Leu Asn Val Asn Val Lys Ser Leu
            260                 265                 270

GCA TAT ATT TTA AGG ATG AAT CGG TAC ATC TGT ACA AGG AAC TGG AAA      864
Ala Tyr Ile Leu Arg Met Asn Arg Tyr Ile Cys Thr Arg Asn Trp Lys
        275                 280                 285

AAA ATC GAG TTA GCT ATC GAT AAA TGT ATA GAA ATC GCC ATT CAG CTT      912
Lys Ile Glu Leu Ala Ile Asp Lys Cys Ile Glu Ile Ala Ile Gln Leu
    290                 295                 300

GGC TGG TTA TCT AGA AGA AAA CGC ATT GAA TTT CTG GAT TCT TCT AAA      960
Gly Trp Leu Ser Arg Arg Lys Arg Ile Glu Phe Leu Asp Ser Ser Lys
305                 310                 315                 320

CTC TCT AAA AAA GAA ATT CTA TAT CTA AAT AAA GAG CGC TTT GAA GAA     1008
Leu Ser Lys Lys Glu Ile Leu Tyr Leu Asn Lys Glu Arg Phe Glu Glu
                325                 330                 335

ATA ACT AAG AAA TCT AAA GAA CAA ATG GAA CAA TTA GAA CAA GAA TCT     1056
Ile Thr Lys Lys Ser Lys Glu Gln Met Glu Gln Leu Glu Gln Glu Ser
            340                 345                 350

ATT AAT TAA                                                          1065
Ile Asn
```

(2) INFORMATION FOR SEQ ID NO:10:

(i) SEQUENCE CHARACTERISTICS:
        (A) LENGTH: 354 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Asn Tyr Ser Asn Cys His Phe Ile Lys Ser Pro Ile His Leu
1               5                   10                  15

Glu Asn Gln Lys Phe Gly Arg Arg Pro Gly Gln Ser Ile Lys Ile Ser
            20                  25                  30

Pro Lys Leu Ala Gln Asn Gly Met Val Glu Val Ile Gly Leu Asp Phe
        35                  40                  45

Leu Ser Ser His Tyr His Ala Leu Ala Ala Ile Gln Arg Leu Leu Thr
    50                  55                  60

Ala Thr Asn Tyr Lys Gly Asn Thr Lys Gly Val Val Leu Ser Arg Glu
65                  70                  75                  80

Ser Asn Ser Phe Gln Phe Glu Gly Trp Ile Pro Arg Ile Arg Phe Thr
                85                  90                  95

Lys Thr Glu Phe Leu Glu Ala Tyr Gly Val Lys Arg Tyr Lys Thr Ser
            100                 105                 110

Arg Asn Lys Tyr Glu Phe Ser Gly Lys Glu Ala Glu Thr Ala Leu Glu
        115                 120                 125

Ala Leu Tyr His Leu Gly His Gln Pro Phe Leu Ile Val Ala Thr Arg
    130                 135                 140

Thr Arg Trp Thr Asn Gly Thr Gln Ile Val Asp Arg Tyr Gln Thr Leu
145                 150                 155                 160

Ser Pro Ile Ile Arg Ile Tyr Glu Gly Trp Glu Gly Leu Thr Asp Glu
```

-continued

```
                165                 170                 175
Glu Asn Ile Asp Ile Asp Leu Thr Pro Phe Asn Ser Pro Pro Thr Arg
            180                 185                 190

Lys His Lys Gly Phe Val Val Glu Pro Cys Pro Ile Leu Val Asp Gln
        195                 200                 205

Ile Glu Ser Tyr Phe Val Ile Lys Pro Ala Asn Val Tyr Gln Glu Ile
    210                 215                 220

Lys Met Arg Phe Pro Asn Ala Ser Lys Tyr Ala Tyr Thr Phe Ile Asp
225                 230                 235                 240

Trp Val Ile Thr Ala Ala Lys Lys Arg Lys Leu Thr Lys Asp
                245                 250                 255

Asn Ser Trp Pro Glu Asn Leu Leu Leu Asn Val Asn Val Lys Ser Leu
            260                 265                 270

Ala Tyr Ile Leu Arg Met Asn Arg Tyr Ile Cys Thr Arg Asn Trp Lys
        275                 280                 285

Lys Ile Glu Leu Ala Ile Asp Lys Cys Ile Glu Ile Ala Ile Gln Leu
    290                 295                 300

Gly Trp Leu Ser Arg Arg Lys Arg Ile Glu Phe Leu Asp Ser Ser Lys
305                 310                 315                 320

Leu Ser Lys Lys Glu Ile Leu Tyr Leu Asn Lys Glu Arg Phe Glu Glu
                325                 330                 335

Ile Thr Lys Lys Ser Lys Glu Gln Met Glu Gln Leu Glu Gln Glu Ser
            340                 345                 350

Ile Asn
```

(2) INFORMATION FOR SEQ ID NO:11:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..795

(xi) SEQUENCE DESCRIPTION: SEQ ID NO:11:

```
ATG GGA AAT TCT GGT TTT TAT TTG TAT AAC ACT GAA AAC TGC GTC TTT     48
Met Gly Asn Ser Gly Phe Tyr Leu Tyr Asn Thr Glu Asn Cys Val Phe
 1               5                  10                  15

GCT GAT AAT ATC AAA GTT GGG CAA ATG ACA GAG CCG CTC AAG GAC CAG     96
Ala Asp Asn Ile Lys Val Gly Gln Met Thr Glu Pro Leu Lys Asp Gln
            20                  25                  30

CAA ATA ATC CTT GGG ACA ACA TCA ACA CCT GTC GCA GCC AAA ATG ACA    144
Gln Ile Ile Leu Gly Thr Thr Ser Thr Pro Val Ala Ala Lys Met Thr
        35                  40                  45

GCT TCT GAT GGA ATA TCT TTA ACA GTC TCC AAT AAT TCA TCA ACC AAT    192
Ala Ser Asp Gly Ile Ser Leu Thr Val Ser Asn Asn Ser Ser Thr Asn
50                  55                  60

GCT TCT ATT ACA ATT GGT TTG GAT GCG GAA AAA GCT TAC CAG CTT ATT    240
Ala Ser Ile Thr Ile Gly Leu Asp Ala Glu Lys Ala Tyr Gln Leu Ile
```

```
CTA GAA AAG TTG GGA GAT CAA ATT CTT GAT GGA ATT GCT GAT ACT ATT      288
Leu Glu Lys Leu Gly Asp Gln Ile Leu Asp Gly Ile Ala Asp Thr Ile
                 85                  90                  95

GTT GAT AGT ACA GTC CAA GAT ATT TTA GAC AAA ATC AAA ACA GAC CCT      336
Val Asp Ser Thr Val Gln Asp Ile Leu Asp Lys Ile Lys Thr Asp Pro
            100                 105                 110

TCT CTA GGT TTG TTG AAA GCT TTT AAC AAC TTT CCA ATC ACT AAT AAA      384
Ser Leu Gly Leu Leu Lys Ala Phe Asn Asn Phe Pro Ile Thr Asn Lys
        115                 120                 125

ATT CAA TGC AAC GGG TTA TTC ACT CCC AGT AAC ATT GAA ACT TTA TTA      432
Ile Gln Cys Asn Gly Leu Phe Thr Pro Ser Asn Ile Glu Thr Leu Leu
    130                 135                 140

GGA GGA ACT GAA ATA GGA AAA TTC ACA GTC ACA CCC AAA AGC TCT GGG      480
Gly Gly Thr Glu Ile Gly Lys Phe Thr Val Thr Pro Lys Ser Ser Gly
145                 150                 155                 160

AGC ATG TTC TTA GTC TCA GCA GAT ATT ATT GCA TCA AGA ATG GAA GGC      528
Ser Met Phe Leu Val Ser Ala Asp Ile Ile Ala Ser Arg Met Glu Gly
                165                 170                 175

GGC GTT GTT CTA GCT TTG GTA CGA GAA GGT GAT TCT AAG CCC TGC GCG      576
Gly Val Val Leu Ala Leu Val Arg Glu Gly Asp Ser Lys Pro Cys Ala
            180                 185                 190

ATT AGT TAT GGA TAC TCA TCA GGC ATT CCT AAT TTA TGT AGT CTA AGA      624
Ile Ser Tyr Gly Tyr Ser Ser Gly Ile Pro Asn Leu Cys Ser Leu Arg
        195                 200                 205

ACC AGT ATT ACT AAT ACA GGA TTG ACT CCG ACA ACG TAT TCA TTA CGT      672
Thr Ser Ile Thr Asn Thr Gly Leu Thr Pro Thr Thr Tyr Ser Leu Arg
    210                 215                 220

GTA GGC GGT TTA GAA AGC GGT GTG GTA TGG GTT AAT GCC CTT TCT AAT      720
Val Gly Gly Leu Glu Ser Gly Val Val Trp Val Asn Ala Leu Ser Asn
225                 230                 235                 240

GGC AAT GAT ATT TTA GGA ATA ACA AAT ACT TCT AAT GTA TCT TTT TTA      768
Gly Asn Asp Ile Leu Gly Ile Thr Asn Thr Ser Asn Val Ser Phe Leu
                245                 250                 255

GAG GTA ATA CCT CAA ACA AAC GCT TAA                                  795
Glu Val Ile Pro Gln Thr Asn Ala
                260                 265

(2) INFORMATION FOR SEQ ID NO:12:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:12:

Met Gly Asn Ser Gly Phe Tyr Leu Tyr Asn Thr Glu Asn Cys Val Phe
 1               5                  10                  15

Ala Asp Asn Ile Lys Val Gly Gln Met Thr Glu Pro Leu Lys Asp Gln
            20                  25                  30

Gln Ile Ile Leu Gly Thr Thr Ser Thr Pro Val Ala Ala Lys Met Thr
        35                  40                  45

Ala Ser Asp Gly Ile Ser Leu Thr Val Ser Asn Ser Ser Thr Asn
    50                  55                  60

Ala Ser Ile Thr Ile Gly Leu Asp Ala Glu Lys Ala Tyr Gln Leu Ile
65                  70                  75                  80

Leu Glu Lys Leu Gly Asp Gln Ile Leu Asp Gly Ile Ala Asp Thr Ile
                85                  90                  95
```

```
Val Asp Ser Thr Val Gln Asp Ile Leu Asp Lys Ile Lys Thr Asp Pro
            100                 105                 110

Ser Leu Gly Leu Leu Lys Ala Phe Asn Asn Phe Pro Ile Thr Asn Lys
        115                 120                 125

Ile Gln Cys Asn Gly Leu Phe Thr Pro Ser Asn Ile Glu Thr Leu Leu
    130                 135                 140

Gly Gly Thr Glu Ile Gly Lys Phe Thr Val Thr Pro Lys Ser Ser Gly
145                 150                 155                 160

Ser Met Phe Leu Val Ser Ala Asp Ile Ile Ala Ser Arg Met Glu Gly
                165                 170                 175

Gly Val Val Leu Ala Leu Val Arg Glu Gly Asp Ser Lys Pro Cys Ala
            180                 185                 190

Ile Ser Tyr Gly Tyr Ser Ser Gly Ile Pro Asn Leu Cys Ser Leu Arg
        195                 200                 205

Thr Ser Ile Thr Asn Thr Gly Leu Thr Pro Thr Thr Tyr Ser Leu Arg
    210                 215                 220

Val Gly Gly Leu Glu Ser Gly Val Val Trp Val Asn Ala Leu Ser Asn
225                 230                 235                 240

Gly Asn Asp Ile Leu Gly Ile Thr Asn Thr Ser Asn Val Ser Phe Leu
                245                 250                 255

Glu Val Ile Pro Gln Thr Asn Ala
            260

(2) INFORMATION FOR SEQ ID NO:13:

(i) SEQUENCE CHARACTERISTICS:
        (A) LENGTH: 309 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..309

(xi) SEQUENCE DESCRIPTION: SEQ ID NO:13:

ATG CAA AAT AAA AGA AAA GTG AGG GAC GAT TTT ATT AAA ATT GTT AAA        48
Met Gln Asn Lys Arg Lys Val Arg Asp Asp Phe Ile Lys Ile Val Lys
  1               5                  10                  15

GAT GTA AAA AAA GAT TTC CCC GAA TTA GAC CTA AAA ATA CGA GTA AAC        96
Asp Val Lys Lys Asp Phe Pro Glu Leu Asp Leu Lys Ile Arg Val Asn
                 20                  25                  30

AAG GAA AAA GTA ACT TTC TTA AAT TCT CCC TTA GAA CTC TAC CAT AAA       144
Lys Glu Lys Val Thr Phe Leu Asn Ser Pro Leu Glu Leu Tyr His Lys
             35                  40                  45

AGT GTC TCA CTA ATT CTA GGA CTG CTT CAA CAA ATA GAA AAC TCT TTA       192
Ser Val Ser Leu Ile Leu Gly Leu Leu Gln Gln Ile Glu Asn Ser Leu
         50                  55                  60

GGA TTA TTC CCA GAC TCT CCT GTT CTT GAA AAA TTA GAG GAT AAC AGT       240
Gly Leu Phe Pro Asp Ser Pro Val Leu Glu Lys Leu Glu Asp Asn Ser
 65                  70                  75                  80

TTA AAG CTA AAA AAG GCT TTG ATT ATG CTT ATC TTG TCT AGA AAA GAC       288
```

```
Leu Lys Leu Lys Lys Ala Leu Ile Met Leu Ile Leu Ser Arg Lys Asp
            85                  90                  95

ATG TTT TCC AAG GCT GAA TAG                                              309
Met Phe Ser Lys Ala Glu
            100
```

(2) INFORMATION FOR SEQ ID NO:14:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:14:

```
Met Gln Asn Lys Arg Lys Val Arg Asp Asp Phe Ile Lys Ile Val Lys
 1               5                  10                  15

Asp Val Lys Lys Asp Phe Pro Glu Leu Asp Leu Lys Ile Arg Val Asn
            20                  25                  30

Lys Glu Lys Val Thr Phe Leu Asn Ser Pro Leu Glu Leu Tyr His Lys
            35                  40                  45

Ser Val Ser Leu Ile Leu Gly Leu Leu Gln Gln Ile Glu Asn Ser Leu
        50                  55                  60

Gly Leu Phe Pro Asp Ser Pro Val Leu Glu Lys Leu Glu Asp Asn Ser
 65                 70                  75                  80

Leu Lys Leu Lys Lys Ala Leu Ile Met Leu Ile Leu Ser Arg Lys Asp
            85                  90                  95

Met Phe Ser Lys Ala Glu
            100
```

(2) INFORMATION FOR SEQ ID NO:15:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..795

(xi) SEQUENCE DESCRIPTION: SEQ ID NO:15:

```
TTG CAC ACC TTA GTT TTT TGC TCT TTT AAG GGA GGA ACT GGA AAA ACA          48
Leu His Thr Leu Val Phe Cys Ser Phe Lys Gly Gly Thr Gly Lys Thr
 1               5                  10                  15

ACA CTT TCT CTA AAC GTG GGA TGC AAC TTG GCC CAA TTT TTA GGG AAA          96
Thr Leu Ser Leu Asn Val Gly Cys Asn Leu Ala Gln Phe Leu Gly Lys
            20                  25                  30

AAA GTG TTA CTT GCT GAC CTA GAC CCG CAA TCC AAT TTA TCT TCT GGA         144
Lys Val Leu Leu Ala Asp Leu Asp Pro Gln Ser Asn Leu Ser Ser Gly
            35                  40                  45

TTG GGG GCT AGT GTC AGA AGT GAC CAA AAA GGC TTG CAC GAC ATA GTA         192
Leu Gly Ala Ser Val Arg Ser Asp Gln Lys Gly Leu His Asp Ile Val
        50                  55                  60
```

```
TAC ACA TCA AAC GAT TTA AAA TCA ATC ATT TGC GAA ACA AAA AAA GAT        240
Tyr Thr Ser Asn Asp Leu Lys Ser Ile Ile Cys Glu Thr Lys Lys Asp
 65              70                  75                  80

AGT GTG GAC CTA ATT CCT GCA TCA TTT TCA TCC GAA CAG TTT AGA GAA        288
Ser Val Asp Leu Ile Pro Ala Ser Phe Ser Ser Glu Gln Phe Arg Glu
             85                  90                  95

TTG GAT ATT CAT AGA GGA CCT AGT AAC AAC TTA AAG TTA TTT CTG AAT        336
Leu Asp Ile His Arg Gly Pro Ser Asn Asn Leu Lys Leu Phe Leu Asn
                100                 105                 110

GAG TAC TGC GCT CCT TTT TAT GAC ATC TGC ATA ATA GAC ACT CCA CCT        384
Glu Tyr Cys Ala Pro Phe Tyr Asp Ile Cys Ile Ile Asp Thr Pro Pro
            115                 120                 125

AGC CTA GGA GGG TTA ACG AAA GAA GCT TTT GTT GCA GGA GAC AAA TTA        432
Ser Leu Gly Gly Leu Thr Lys Glu Ala Phe Val Ala Gly Asp Lys Leu
130                 135                 140

ATT GCT TGT TTA ACT CCA GAA CCT TTT TCT ATT CTA GGG TTA CAA AAG        480
Ile Ala Cys Leu Thr Pro Glu Pro Phe Ser Ile Leu Gly Leu Gln Lys
145                 150                 155                 160

ATA CGT GAA TTC TTA AGT TCG GTC GGA AAA CCT GAA GAA GAA CAC ATT        528
Ile Arg Glu Phe Leu Ser Ser Val Gly Lys Pro Glu Glu Glu His Ile
                165                 170                 175

CTT GGA ATA GCT TTG TCT TTT TGG GAT GAT CGT AAC TCG ACT AAC CAA        576
Leu Gly Ile Ala Leu Ser Phe Trp Asp Asp Arg Asn Ser Thr Asn Gln
            180                 185                 190

ATG TAT ATA GAC ATT ATC GAG TCT ATT TAC AAA AAC AAG CTT TTT TCA        624
Met Tyr Ile Asp Ile Ile Glu Ser Ile Tyr Lys Asn Lys Leu Phe Ser
        195                 200                 205

ACA AAA ATT CGT CGA GAT ATT TCT CTC AGC CGT TCT CTT CTT AAA GAA        672
Thr Lys Ile Arg Arg Asp Ile Ser Leu Ser Arg Ser Leu Leu Lys Glu
210                 215                 220

GAT TCT GTA GCT AAT GTC TAT CCA AAT TCT AGG GCC GCA GAA GAT ATT        720
Asp Ser Val Ala Asn Val Tyr Pro Asn Ser Arg Ala Ala Glu Asp Ile
225                 230                 235                 240

CTG AAG TTA ACG CAT GAA ATA GCA AAT ATT TTG CAT ATC GAA TAT GAA        768
Leu Lys Leu Thr His Glu Ile Ala Asn Ile Leu His Ile Glu Tyr Glu
                245                 250                 255

CGA GAT TAC TCT CAG AGG ACA ACG TGA                                    795
Arg Asp Tyr Ser Gln Arg Thr Thr
            260                 265

(2) INFORMATION FOR SEQ ID NO:16:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:16:

Leu His Thr Leu Val Phe Cys Ser Phe Lys Gly Gly Thr Gly Lys Thr
  1               5                  10                  15

Thr Leu Ser Leu Asn Val Gly Cys Asn Leu Ala Gln Phe Leu Gly Lys
             20                  25                  30

Lys Val Leu Leu Ala Asp Leu Asp Pro Gln Ser Asn Leu Ser Ser Gly
         35                  40                  45

Leu Gly Ala Ser Val Arg Ser Asp Gln Lys Gly Leu His Asp Ile Val
     50                  55                  60

Tyr Thr Ser Asn Asp Leu Lys Ser Ile Ile Cys Glu Thr Lys Lys Asp
 65              70                  75                  80
```

```
Ser Val Asp Leu Ile Pro Ala Ser Phe Ser Ser Glu Gln Phe Arg Glu
                85                  90                  95

Leu Asp Ile His Arg Gly Pro Ser Asn Asn Leu Lys Leu Phe Leu Asn
            100                 105                 110

Glu Tyr Cys Ala Pro Phe Tyr Asp Ile Cys Ile Ile Asp Thr Pro Pro
            115                 120                 125

Ser Leu Gly Gly Leu Thr Lys Glu Ala Phe Val Ala Gly Asp Lys Leu
    130                 135                 140

Ile Ala Cys Leu Thr Pro Glu Pro Phe Ser Ile Leu Gly Leu Gln Lys
145                 150                 155                 160

Ile Arg Glu Phe Leu Ser Ser Val Gly Lys Pro Glu Glu His Ile
                165                 170                 175

Leu Gly Ile Ala Leu Ser Phe Trp Asp Asp Arg Asn Ser Thr Asn Gln
            180                 185                 190

Met Tyr Ile Asp Ile Ile Glu Ser Ile Tyr Lys Asn Lys Leu Phe Ser
            195                 200                 205

Thr Lys Ile Arg Arg Asp Ile Ser Leu Ser Arg Ser Leu Leu Lys Glu
    210                 215                 220

Asp Ser Val Ala Asn Val Tyr Pro Asn Ser Arg Ala Ala Glu Asp Ile
225                 230                 235                 240

Leu Lys Leu Thr His Glu Ile Ala Asn Ile Leu His Ile Glu Tyr Glu
                245                 250                 255

Arg Asp Tyr Ser Gln Arg Thr Thr
            260
```

(2) INFORMATION FOR SEQ ID NO:17:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..744

(xi) SEQUENCE DESCRIPTION: SEQ ID NO:17:

```
GTG AAC AAA CTA AAA AAA GAA GCG GAT GTC TTT TTT AAA AAA AAT CAA      48
Val Asn Lys Leu Lys Lys Glu Ala Asp Val Phe Phe Lys Lys Asn Gln
 1               5                  10                  15

ACT GCC GCT TCT CTA GAT TTT AAG AAG ACG CTT CCC TCC ATT GAA CTA      96
Thr Ala Ala Ser Leu Asp Phe Lys Lys Thr Leu Pro Ser Ile Glu Leu
            20                  25                  30

TTC TCA GCA ACT TTG AAT TCT GAG GAA AGT CAG AGT TTG GAT CGA TTA     144
Phe Ser Ala Thr Leu Asn Ser Glu Glu Ser Gln Ser Leu Asp Arg Leu
        35                  40                  45

TTT TTA TCA GAG TCC CAA AAC TAT TCG GAT GAA GAA TTT TAT CAA GAA     192
Phe Leu Ser Glu Ser Gln Asn Tyr Ser Asp Glu Glu Phe Tyr Gln Glu
 50                  55                  60

GAC ATC CTA GCG GTA AAA CTG CTT ACT GGT CAG ATA AAA TCC ATA CAG     240
Asp Ile Leu Ala Val Lys Leu Leu Thr Gly Gln Ile Lys Ser Ile Gln
```

```
                65                   70                  75                  80
AAG CAA CAC GTA CTT CTT TTA GGA GAA AAA ATC TAT AAT GCT AGA AAA                288
Lys Gln His Val Leu Leu Leu Gly Glu Lys Ile Tyr Asn Ala Arg Lys
                    85                  90                  95

ATC CTG AGT AAG GAT CAC TTC TCC TCA ACA ACT TTT TCA TCT TGG ATA                336
Ile Leu Ser Lys Asp His Phe Ser Ser Thr Thr Phe Ser Ser Trp Ile
            100                 105                 110

GAG TTA GTT TTT AGA ACT AAG TCT TCT GCT TAC AAT GCT CTT GCA TAT                384
Glu Leu Val Phe Arg Thr Lys Ser Ser Ala Tyr Asn Ala Leu Ala Tyr
            115                 120                 125

TAC GAG CTT TTT ATA AAC CTC CCC AAC CAA ACT CTA CAA AAA GAG TTT                432
Tyr Glu Leu Phe Ile Asn Leu Pro Asn Gln Thr Leu Gln Lys Glu Phe
        130                 135                 140

CAA TCG ATC CCC TAT AAA TCC GCA TAT ATT TTG GCC GCT AGA AAA GGC                480
Gln Ser Ile Pro Tyr Lys Ser Ala Tyr Ile Leu Ala Ala Arg Lys Gly
145                 150                 155                 160

GAT TTA AAA ACC AAG GTC GAT GTG ATA GGG AAA GTA TGT GGA ATG TCG                528
Asp Leu Lys Thr Lys Val Asp Val Ile Gly Lys Val Cys Gly Met Ser
                165                 170                 175

AAC TCA TCG GCG ATA AGG GTG TTG GAT CAA TTT CTT CCT TCA TCT AGA                576
Asn Ser Ser Ala Ile Arg Val Leu Asp Gln Phe Leu Pro Ser Ser Arg
            180                 185                 190

AAC AAA GAC GTT AGA GAA ACG ATA GAT AAG TCT GAT TCA GAG AAG AAT                624
Asn Lys Asp Val Arg Glu Thr Ile Asp Lys Ser Asp Ser Glu Lys Asn
            195                 200                 205

CGC CAA TTA TCT GAT TTC TTA ATA GAG ATA CTT CGC ATC ATG TGT TCC                672
Arg Gln Leu Ser Asp Phe Leu Ile Glu Ile Leu Arg Ile Met Cys Ser
        210                 215                 220

GGA GTT TCT TTG TCC TCC TAT AAC GAA AAT CTT CTA CAA CAG CTT TTT                720
Gly Val Ser Leu Ser Ser Tyr Asn Glu Asn Leu Leu Gln Gln Leu Phe
225                 230                 235                 240

GAA CTT TTT AAG CAA AAG AGC TGA                                                744
Glu Leu Phe Lys Gln Lys Ser
                245

(2) INFORMATION FOR SEQ ID NO:18:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:18:

Val Asn Lys Leu Lys Lys Glu Ala Asp Val Phe Phe Lys Lys Asn Gln
1               5                   10                  15

Thr Ala Ala Ser Leu Asp Phe Lys Lys Thr Leu Pro Ser Ile Glu Leu
            20                  25                  30

Phe Ser Ala Thr Leu Asn Ser Glu Glu Ser Gln Ser Leu Asp Arg Leu
        35                  40                  45

Phe Leu Ser Glu Ser Gln Asn Tyr Ser Asp Glu Phe Tyr Gln Glu
    50                  55                  60

Asp Ile Leu Ala Val Lys Leu Leu Thr Gly Gln Ile Lys Ser Ile Gln
65                  70                  75                  80

Lys Gln His Val Leu Leu Leu Gly Glu Lys Ile Tyr Asn Ala Arg Lys
                85                  90                  95

Ile Leu Ser Lys Asp His Phe Ser Thr Thr Phe Ser Ser Trp Ile
            100                 105                 110
```

```
Glu Leu Val Phe Arg Thr Lys Ser Ser Ala Tyr Asn Ala Leu Ala Tyr
            115                 120                 125

Tyr Glu Leu Phe Ile Asn Leu Pro Asn Gln Thr Leu Gln Lys Glu Phe
        130                 135                 140

Gln Ser Ile Pro Tyr Lys Ser Ala Tyr Ile Leu Ala Ala Arg Lys Gly
145                 150                 155                 160

Asp Leu Lys Thr Lys Val Asp Val Ile Gly Lys Val Cys Gly Met Ser
                165                 170                 175

Asn Ser Ser Ala Ile Arg Val Leu Asp Gln Phe Leu Pro Ser Ser Arg
            180                 185                 190

Asn Lys Asp Val Arg Glu Thr Ile Asp Lys Ser Asp Ser Glu Lys Asn
        195                 200                 205

Arg Gln Leu Ser Asp Phe Leu Ile Glu Ile Leu Arg Ile Met Cys Ser
    210                 215                 220

Gly Val Ser Leu Ser Ser Tyr Asn Glu Asn Leu Leu Gln Gln Leu Phe
225                 230                 235                 240

Glu Leu Phe Lys Gln Lys Ser
                245

(2) INFORMATION FOR SEQ ID NO:19:

(i) SEQUENCE CHARACTERISTICS:
        (A) LENGTH: 930 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..930

(xi) SEQUENCE DESCRIPTION: SEQ ID NO:19:

TTG GTT AAG AAA ATG GGC TCG ATG GCT TTC CAT AAA AGT AGA TTG TTT      48
Leu Val Lys Lys Met Gly Ser Met Ala Phe His Lys Ser Arg Leu Phe
  1               5                  10                  15

TTA ACT TTT GGG GAC GCG TCG GAA ATT TGG TTA TCT ACT TTA TCT TAT      96
Leu Thr Phe Gly Asp Ala Ser Glu Ile Trp Leu Ser Thr Leu Ser Tyr
                 20                  25                  30

CTA ACT AGA AAA AAT TAT GCG TCT GGG ATT AAC TTT CTT GTT TCT TTA     144
Leu Thr Arg Lys Asn Tyr Ala Ser Gly Ile Asn Phe Leu Val Ser Leu
             35                  40                  45

GAG ATT CTG GAT TTA TCG GAA ACC TTG ATA AAG GCT ATT TCT CTT GAC     192
Glu Ile Leu Asp Leu Ser Glu Thr Leu Ile Lys Ala Ile Ser Leu Asp
         50                  55                  60

CAC AGC GAA TCT TTG TTT AAA ATC AAG TCT CTA GAT GTT TTT AAT GGA     240
His Ser Glu Ser Leu Phe Lys Ile Lys Ser Leu Asp Val Phe Asn Gly
 65                  70                  75                  80

AAA GTT GTT TCA GAG GCA TCT AAA CAG GCT AGA GCG GCA TGC TAC ATA     288
Lys Val Val Ser Glu Ala Ser Lys Gln Ala Arg Ala Ala Cys Tyr Ile
                 85                  90                  95

TCT TTC ACA AAG TTT TTG TAT AGA TTG ACC AAG GGA TAT ATT AAA CCC     336
Ser Phe Thr Lys Phe Leu Tyr Arg Leu Thr Lys Gly Tyr Ile Lys Pro
                100                 105                 110
```

```
GCT ATT CCA TTG AAA GAT TTT GGA AAC ACT ACA TTT TTT AAA ATC CGA        384
Ala Ile Pro Leu Lys Asp Phe Gly Asn Thr Thr Phe Phe Lys Ile Arg
        115                 120                 125

GAC AAA ATC AAA ACA GAA TCG ATT TCT AAG CAG GAA TGG ACA GTT TTT        432
Asp Lys Ile Lys Thr Glu Ser Ile Ser Lys Gln Glu Trp Thr Val Phe
130                 135                 140

TTT GAA GCG CTC CGG ATA GTG AAT TAT AGA GAC TAT TTA ATC GGT AAA        480
Phe Glu Ala Leu Arg Ile Val Asn Tyr Arg Asp Tyr Leu Ile Gly Lys
145                 150                 155                 160

TTG ATT GTA CAA GGG ATC CGT AAG TTA GAC GAA ATT TTG TCT TTG CGC        528
Leu Ile Val Gln Gly Ile Arg Lys Leu Asp Glu Ile Leu Ser Leu Arg
                165                 170                 175

ACA GAC GAT CTA TTT TTT GCA TCC AAT CAG ATT TCC TTT CGC ATT AAA        576
Thr Asp Asp Leu Phe Phe Ala Ser Asn Gln Ile Ser Phe Arg Ile Lys
            180                 185                 190

AAA AGA CAG AAT AAA GAA ACC AAA ATT CTA ATC ACA TTT CCT ATC AGC        624
Lys Arg Gln Asn Lys Glu Thr Lys Ile Leu Ile Thr Phe Pro Ile Ser
        195                 200                 205

TTA ATG GAA GAG TTG CAA AAA TAC ACT TGT GGG AGA AAT GGG AGA GTA        672
Leu Met Glu Glu Leu Gln Lys Tyr Thr Cys Gly Arg Asn Gly Arg Val
210                 215                 220

TTT GTT TCT AAA ATA GGG ATT CCT GTA ACA ACA AGT CAG GTT GCG CAT        720
Phe Val Ser Lys Ile Gly Ile Pro Val Thr Thr Ser Gln Val Ala His
225                 230                 235                 240

AAT TTT AGG CTT GCA GAG TTC CAT AGT GCT ATG AAA ATA AAA ATT ACT        768
Asn Phe Arg Leu Ala Glu Phe His Ser Ala Met Lys Ile Lys Ile Thr
                245                 250                 255

CCC AGA GTA CTT CGT GCA AGC GCT TTG ATT CAT TTA AAG CAA ATA GGA        816
Pro Arg Val Leu Arg Ala Ser Ala Leu Ile His Leu Lys Gln Ile Gly
            260                 265                 270

TTA AAA GAT GAG GAA ATC ATG CGT ATT TCC TGT CTT TCA TCG AGA CAA        864
Leu Lys Asp Glu Glu Ile Met Arg Ile Ser Cys Leu Ser Ser Arg Gln
        275                 280                 285

AGT GTG TGT TCT TAT TGT TCT GGG GAA GAG GTA ATT CCT CTA GTA CAA        912
Ser Val Cys Ser Tyr Cys Ser Gly Glu Glu Val Ile Pro Leu Val Gln
290                 295                 300

ACA CCC ACA ATA TTG TGA                                                930
Thr Pro Thr Ile Leu
305             310
```

(2) INFORMATION FOR SEQ ID NO:20:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:20:

```
Leu Val Lys Lys Met Gly Ser Met Ala Phe His Lys Ser Arg Leu Phe
1               5                   10                  15

Leu Thr Phe Gly Asp Ala Ser Glu Ile Trp Leu Ser Thr Leu Ser Tyr
            20                  25                  30

Leu Thr Arg Lys Asn Tyr Ala Ser Gly Ile Asn Phe Leu Val Ser Leu
        35                  40                  45

Glu Ile Leu Asp Leu Ser Glu Thr Leu Ile Lys Ala Ile Ser Leu Asp
    50                  55                  60

His Ser Glu Ser Leu Phe Lys Ile Lys Ser Leu Asp Val Phe Asn Gly
65                  70                  75                  80
```

```
Lys Val Val Ser Glu Ala Ser Lys Gln Ala Arg Ala Ala Cys Tyr Ile
                85                  90                  95

Ser Phe Thr Lys Phe Leu Tyr Arg Leu Thr Lys Gly Tyr Ile Lys Pro
            100                 105                 110

Ala Ile Pro Leu Lys Asp Phe Gly Asn Thr Thr Phe Phe Lys Ile Arg
            115                 120                 125

Asp Lys Ile Lys Thr Glu Ser Ile Ser Lys Gln Glu Trp Thr Val Phe
130                 135                 140

Phe Glu Ala Leu Arg Ile Val Asn Tyr Arg Asp Tyr Leu Ile Gly Lys
145                 150                 155                 160

Leu Ile Val Gln Gly Ile Arg Lys Leu Asp Glu Ile Leu Ser Leu Arg
                165                 170                 175

Thr Asp Asp Leu Phe Phe Ala Ser Asn Gln Ile Ser Phe Arg Ile Lys
                180                 185                 190

Lys Arg Gln Asn Lys Glu Thr Lys Ile Leu Ile Thr Phe Pro Ile Ser
                195                 200                 205

Leu Met Glu Glu Leu Gln Lys Tyr Thr Cys Gly Arg Asn Gly Arg Val
210                 215                 220

Phe Val Ser Lys Ile Gly Ile Pro Val Thr Thr Ser Gln Val Ala His
225                 230                 235                 240

Asn Phe Arg Leu Ala Glu Phe His Ser Ala Met Lys Ile Lys Ile Thr
                245                 250                 255

Pro Arg Val Leu Arg Ala Ser Ala Leu Ile His Leu Lys Gln Ile Gly
                260                 265                 270

Leu Lys Asp Glu Glu Ile Met Arg Ile Ser Cys Leu Ser Ser Arg Gln
                275                 280                 285

Ser Val Cys Ser Tyr Cys Ser Gly Glu Glu Val Ile Pro Leu Val Gln
                290                 295                 300

Thr Pro Thr Ile Leu
305
```

(2) INFORMATION FOR SEQ ID NO:21:

(i) SEQUENCE CHARACTERISTICS:
        (A) LENGTH: 993 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis
        (B) STRAIN: GO/86 serotype D ( trachoma biovar )

(vii) IMMEDIATE SOURCE:
        (B) CLONE: pUC8-pGO plasmid, ATCC 68314

(ix) FEATURE:
        (A) NAME/KEY: CDS
        (B) LOCATION: 1..993

(xi) SEQUENCE DESCRIPTION: SEQ ID NO:21:

```
ATG GGT AAA GGG ATT TTA TCT TTG CAG CAA GAA ATG TCG TTA GAA TAT    48
Met Gly Lys Gly Ile Leu Ser Leu Gln Gln Glu Met Ser Leu Glu Tyr
1               5                   10                  15

AGT GAA AAG TCT TAT CAG GAA GTT TTA AAA ATT CGC CAA GAA TCC TAT    96
Ser Glu Lys Ser Tyr Gln Glu Val Leu Lys Ile Arg Gln Glu Ser Tyr
            20                  25                  30

TGG AAA CGC ATG AAA AGC TTC TCC TTA TTC GAA GTT ATT ATG CAT TGG    144
Trp Lys Arg Met Lys Ser Phe Ser Leu Phe Glu Val Ile Met His Trp
```

```
                35                    40                      45
ACC GCA TCA CTC AAC AAA CAT ACT TGT AGA TCA TAT CGA GGA TCT TTT       192
Thr Ala Ser Leu Asn Lys His Thr Cys Arg Ser Tyr Arg Gly Ser Phe
         50                  55                  60

TTG TCT TTA GAA AAG ATT GGT CTA TTG TCC TTG GAT ATG AAT CTG CAA       240
Leu Ser Leu Glu Lys Ile Gly Leu Leu Ser Leu Asp Met Asn Leu Gln
 65                  70                  75                  80

GAG TTT TCC CTT TTA AAT CAT AAT CTA ATC CTA GAT GCG ATT AAA AAA       288
Glu Phe Ser Leu Leu Asn His Asn Leu Ile Leu Asp Ala Ile Lys Lys
                 85                  90                  95

GTT TCC TCT GCC AAG ACT TCT TGG ACC GAA GGT ACT AAA CAA GTT CGA       336
Val Ser Ser Ala Lys Thr Ser Trp Thr Glu Gly Thr Lys Gln Val Arg
            100                 105                 110

GCA GCA AGC TAT ATT TCC TTA ACA AGA TTC CTA AAC AGG ATG ACT CAA       384
Ala Ala Ser Tyr Ile Ser Leu Thr Arg Phe Leu Asn Arg Met Thr Gln
            115                 120                 125

GGA ATA GTC GCT ATA GCG CAA CCT TCT AAA CAA GAA AAT AGT CGA ACA       432
Gly Ile Val Ala Ile Ala Gln Pro Ser Lys Gln Glu Asn Ser Arg Thr
130                 135                 140

TTT TTT AAA ACC AGG GAA ATA GTA AAA ACG GAT GCG ATG AAC AGT TTG       480
Phe Phe Lys Thr Arg Glu Ile Val Lys Thr Asp Ala Met Asn Ser Leu
145                 150                 155                 160

CAA ACA GCA TCC TTC CTA AAA GAG CTA AAA AAA ATC AAT GCC CGG GAT       528
Gln Thr Ala Ser Phe Leu Lys Glu Leu Lys Lys Ile Asn Ala Arg Asp
                165                 170                 175

TGG TTG ATC GCC CAG ACA ATG CTC CAA GGA GGT AAA CGC TCC TCT GAA       576
Trp Leu Ile Ala Gln Thr Met Leu Gln Gly Gly Lys Arg Ser Ser Glu
            180                 185                 190

GTC TTA AGC TTG GAG ATT AGT CAG ATT TGT TTC CAA CAA GCT ACC ATT       624
Val Leu Ser Leu Glu Ile Ser Gln Ile Cys Phe Gln Gln Ala Thr Ile
            195                 200                 205

TCT TTC TCC CAG CTT AAG AAC CGT CAG ACA GAA AAG AGG ATT ATT ATA       672
Ser Phe Ser Gln Leu Lys Asn Arg Gln Thr Glu Lys Arg Ile Ile Ile
            210                 215                 220

ACT TAT CCT CAG AAG TTT ATG CAC TTT CTA CAA GAG TAC ATC GGT CAA       720
Thr Tyr Pro Gln Lys Phe Met His Phe Leu Gln Glu Tyr Ile Gly Gln
225                 230                 235                 240

CGA AGA GGT TTT GTC TTC GTA ACT CGC TCC GGA AAA ATG GTG GGG TTA       768
Arg Arg Gly Phe Val Phe Val Thr Arg Ser Gly Lys Met Val Gly Leu
                245                 250                 255

AGG CAA ATC GCC CGC ACG TTC TCT CAA GCA GGA CTA CAA GCT GCA ATC       816
Arg Gln Ile Ala Arg Thr Phe Ser Gln Ala Gly Leu Gln Ala Ala Ile
            260                 265                 270

CCT TTT AAA ATA ACC CCG CAC GTG CTT CGA GCA ACC GCT GTG ACG GAG       864
Pro Phe Lys Ile Thr Pro His Val Leu Arg Ala Thr Ala Val Thr Glu
            275                 280                 285

TAC AAA CGC CTA GGG TGC TCA GAC TCC GAC ATA ATG AAG GTC ACA GGA       912
Tyr Lys Arg Leu Gly Cys Ser Asp Ser Asp Ile Met Lys Val Thr Gly
            290                 295                 300

CAC GCA ACC GCA AAG ATG ATA TTT GCG TAC GAT AAA TCT TCT CGA GAA       960
His Ala Thr Ala Lys Met Ile Phe Ala Tyr Asp Lys Ser Ser Arg Glu
305                 310                 315                 320

GAC AAC GCT TCA AAG AAG ATG GCT CTA ATA TAG                            993
Asp Asn Ala Ser Lys Lys Met Ala Leu Ile
                325                 330
```

(2) INFORMATION FOR SEQ ID NO:22:

(i) SEQUENCE CHARACTERISTICS:
        (A) LENGTH: 330 amino acids (B) TYPE: amino acid
        (D) TOPOLOGY: linear (ii) MOLECULE TYPE: protein (xi) SEQUENCE DESCRIPTION: SEQ ID NO:22:

Met Gly Lys Gly Ile Leu Ser Leu Gln Gln Glu Met Ser Leu Glu Tyr
 1               5                  10                  15

Ser Glu Lys Ser Tyr Gln Glu Val Leu Lys Ile Arg Gln Glu Ser Tyr
                20                  25                  30

Trp Lys Arg Met Lys Ser Phe Ser Leu Phe Glu Val Ile Met His Trp
            35                  40                  45

Thr Ala Ser Leu Asn Lys His Thr Cys Arg Ser Tyr Arg Gly Ser Phe
        50                  55                  60

Leu Ser Leu Glu Lys Ile Gly Leu Leu Ser Leu Asp Met Asn Leu Gln
 65                  70                  75                  80

Glu Phe Ser Leu Leu Asn His Asn Leu Ile Leu Asp Ala Ile Lys Lys
                85                  90                  95

Val Ser Ser Ala Lys Thr Ser Trp Thr Glu Gly Thr Lys Gln Val Arg
            100                 105                 110

Ala Ala Ser Tyr Ile Ser Leu Thr Arg Phe Leu Asn Arg Met Thr Gln
        115                 120                 125

Gly Ile Val Ala Ile Ala Gln Pro Ser Lys Gln Glu Asn Ser Arg Thr
130                 135                 140

Phe Phe Lys Thr Arg Glu Ile Val Lys Thr Asp Ala Met Asn Ser Leu
145                 150                 155                 160

Gln Thr Ala Ser Phe Leu Lys Glu Leu Lys Lys Ile Asn Ala Arg Asp
                165                 170                 175

Trp Leu Ile Ala Gln Thr Met Leu Gln Gly Gly Lys Arg Ser Ser Glu
            180                 185                 190

Val Leu Ser Leu Glu Ile Ser Gln Ile Cys Phe Gln Gln Ala Thr Ile
        195                 200                 205

Ser Phe Ser Gln Leu Lys Asn Arg Gln Thr Glu Lys Arg Ile Ile Ile
210                 215                 220

Thr Tyr Pro Gln Lys Phe Met His Phe Leu Gln Glu Tyr Ile Gly Gln
225                 230                 235                 240

Arg Arg Gly Phe Val Phe Val Thr Arg Ser Gly Lys Met Val Gly Leu
                245                 250                 255

Arg Gln Ile Ala Arg Thr Phe Ser Gln Ala Gly Leu Gln Ala Ala Ile
            260                 265                 270

Pro Phe Lys Ile Thr Pro His Val Leu Arg Ala Thr Ala Val Thr Glu
        275                 280                 285

Tyr Lys Arg Leu Gly Cys Ser Asp Ser Asp Ile Met Lys Val Thr Gly
290                 295                 300

His Ala Thr Ala Lys Met Ile Phe Ala Tyr Asp Lys Ser Ser Arg Glu
305                 310                 315                 320

Asp Asn Ala Ser Lys Lys Met Ala Leu Ile
                325                 330

(2) INFORMATION FOR SEQ ID NO:23:

(i) SEQUENCE CHARACTERISTICS:
        (A) LENGTH: 370 amino acids
        (B) TYPE: amino acid
        (D) TOPOLOGY: linear (ii) MOLECULE TYPE: protein (vi) ORIGINAL SOURCE:
             (B) STRAIN: E. coli ATCC 68315

(vii) IMMEDIATE SOURCE:
             (B) CLONE: plasmid P03/GO/MC1

(ix) FEATURE:
             (A) NAME/KEY: Region
             (B) LOCATION: 1..370
             (D) OTHER INFORMATION: /label= polypeptide
                 /note= "polypeptide is a fusion protein of the
                 RNA-polymerase from bacteriophage MS2 and the
                 protein encoded by the ORF3D gene of C.

(ix) FEATURE:
             (A) NAME/KEY: Region
             (B) LOCATION: 107..370
             (D) OTHER INFORMATION: /label= region
                 /note= "this portion of the fusion protein is the
                 protein encoded by the ORF3D gene."

(ix) FEATURE:
             (A) NAME/KEY: Region
             (B) LOCATION: 1..106
             (D) OTHER INFORMATION: /label= region
                 /note= "this portion of the fusion protein is a
                 fragment of the RNA polymerase gene from the
                 bacteriophage MS2."

(xi) SEQUENCE DESCRIPTION: SEQ ID NO:23:

```
Met Ser Lys Thr Thr Lys Lys Phe Asn Ser Leu Cys Ile Asp Leu Pro
1               5                  10                  15

Arg Asp Leu Ser Leu Glu Ile Tyr Gln Ser Ile Ala Ser Val Ala Thr
            20                  25                  30

Gly Ser Gly Asp Pro His Ser Asp Asp Phe Thr Ala Ile Ala Tyr Leu
        35                  40                  45

Arg Asp Glu Leu Leu Thr Lys His Pro Thr Leu Gly Ser Gly Asn Asp
50                  55                  60

Glu Ala Thr Arg Arg Thr Leu Ala Ile Ala Lys Leu Arg Glu Ala Asn
65                  70                  75                  80

Gly Asp Arg Gly Gln Ile Asn Arg Glu Gly Phe Leu His Asp Lys Ser
                85                  90                  95

Leu Ser Trp Asp Ile Arg Ala Thr Gly Ser Met Gly Asn Ser Gly Phe
            100                 105                 110

Tyr Leu Tyr Asn Thr Glu Asn Cys Val Phe Ala Asp Asn Ile Lys Val
        115                 120                 125

Gly Gln Met Thr Glu Pro Leu Lys Asp Gln Gln Ile Ile Leu Gly Thr
130                 135                 140

Thr Ser Thr Pro Val Ala Ala Lys Met Thr Ala Ser Asp Gly Ile Ser
145                 150                 155                 160

Leu Thr Val Ser Asn Asn Ser Ser Thr Asn Ala Ser Ile Thr Ile Gly
                165                 170                 175

Leu Asp Ala Glu Lys Ala Tyr Gln Leu Ile Leu Glu Lys Leu Gly Asp
            180                 185                 190

Gln Ile Leu Asp Gly Ile Ala Asp Thr Ile Val Asp Ser Thr Val Gln
        195                 200                 205

Asp Ile Leu Asp Lys Ile Lys Thr Asp Pro Ser Leu Gly Leu Leu Lys
210                 215                 220

Ala Phe Asn Asn Phe Pro Ile Thr Asn Lys Ile Gln Cys Asn Gly Leu
225                 230                 235                 240

Phe Thr Pro Ser Asn Ile Glu Thr Leu Leu Gly Gly Thr Glu Ile Gly
                245                 250                 255
```

-continued

```
Lys Phe Thr Val Thr Pro Lys Ser Ser Gly Ser Met Phe Leu Val Ser
            260                 265                 270

Ala Asp Ile Ile Ala Ser Arg Met Glu Gly Gly Val Val Leu Ala Leu
        275                 280                 285

Val Arg Glu Gly Asp Ser Lys Pro Cys Ala Ile Ser Tyr Gly Tyr Ser
    290                 295                 300

Ser Gly Ile Pro Asn Leu Cys Ser Leu Arg Thr Ser Ile Thr Asn Thr
305                 310                 315                 320

Gly Leu Thr Pro Thr Thr Tyr Ser Leu Arg Val Gly Gly Leu Glu Ser
                325                 330                 335

Gly Val Val Trp Val Asn Ala Leu Ser Asn Gly Asn Asp Ile Leu Gly
            340                 345                 350

Ile Thr Asn Thr Ser Asn Val Ser Phe Leu Glu Val Ile Pro Gln Thr
        355                 360                 365

Asn Ala
    370
```

We claim:

1. A pCTD plasmid isolated from *Chlamydia trachomatis* serotype D comprising the following nucleotide sequence:

```
       10                   30       SEQ ID NO:6
ATATTCATATTCTGTTGCCAGAAAAAACAC

50
CTTTAGGCTATATTAGAGCCATCTTCTTTG 70                   90
AAGCGTTGTCTTCTCGAGAAGATTTATCGT

110
ACGCAAATATCATCTTTGCGGTTGCGTGTC 130                  150
CTGTGACCTTCATTATGTCGGAGTCTGAGC

170
ACCCTAGGCGTTTGTACTCCGTCACAGCGG 190                  210
TTGCTCGAAGCACGTGCGGGGTTATTTTAA

230
AAGGGATTGCAGCTTGTAGTCCTGCTTGAG 250                  270
AGAACGTGCGGGCGATTTGCCTTAACCCCA

290
CCATTTTTCCGGAGCGAGTTACGAAGACAA 310                  330
AACCTCTTCGTTGACCGATGTACTCTTGTA

350
GAAAGTGCATAAACTTCTGAGGATAAGTTA 370                  390
TAATAATCCTCTTTTCTGTCTGACGGTTCT

410
TAAGCTGGGAGAAAGAAATGGTAGCTTGTT 430                  450
```

-continued

```
GGAAACAAATCTGACTAATCTCCAAGCTTA

470
AGACTTCAGAGGAGCGTTTACCTCCTTGGA 490                  510
GCATTGTCTGGGCGATCAACCAATCCCGGG

530
CATTGATTTTTTTTAGCTCTTTTAGGAAGG 550                  570
ATGCTGTTTGCAAACTGTTCATCGCATCCG

590
TTTTTACTATTTCCCTGGTTTTAAAAAATG 610                  630
TTCGACTATTTTCTTGTTTAGAAGGTTGCG

650
CTATAGCGACTATTCCTTGAGTCATCCTGT 670                  690
TTAGGAATCTTGTTAAGGAAATATAGCTTG

710
CTGCTCGAACTTGTTTAGTACCTTCGGTCC 730                  750
AAGAAGTCTTGGCAGAGGAAACTTTTTTAA

770
TCGCATCTAGGATTAGATTATGATTTAAAA 790                  810
GGGAAAACTCTTGCAGATTCATATCCAAGG

830
ACAATAGACCAATCTTTTCTAAAGACAAAA 850                  870
AAGATCCTCGATATGATCTACAAGTATGTT

890
TGTTGAGTGATGCGGTCCAATGCATAATAA 910                  930

-continued
CTTCGAATAAGGAGAAGCTTTTCATGCGTT

950
TCCAATAGGATTCTTGGCGAATTTTTAAAA 970           990
CTTCCTGATAAGACTTTTCACTATATTCTA

1010
ACGACATTTCTTGCTGCAAAGATAAAATCC 1030           1050
CTTTACCCATGAAATCCCTCGTGATATAAC

1070
CTATCCGTAAAATGTCCTGATTAGTGAAAT 1090           1110
AATCAGGTTGTTAACAGGATAGCACGCTCG

1130
GTATTTTTTATATAAACATGAAAACTCGT
  ORF1 >>

1150           1170
TCCGAAATAGAAAATCGCATGCAAGATATC

1190
GAGTATGCGTTGTTAGGTAAAGCTCTGATA 1210           1230
TTTGAAGACTCTACTGAGTATATTCTGAGG

1250
CAGCTTGCTAATTATGAGTTTAAGTGTTCT 1270           1290
CATCATAAAAACATATTCATAGTATTTAAA

1310
CACTTAAAAGACAATGGATTACCTATAACT 1330           1350
GTAGACTCGGCTTGGGAAGAGCTTTTGCGG

1370
CGTCGTATCAAAGATATGGACAAATCGTAT 1390           1410
CTCGGGTTAATGTTGCATGATGCTTTATCA

1430
AATGACAAGCTTAGATCCGTTTCTCATACG 1450           1470
GTTTTCCTCGATGATTTGAGCGTGTGTAGC

1490
GCTGAAGAAAATTTGAGTAATTTCATTTTC 1510           1530
CGCTCGTTTAATGAGTACAATGAAAATCCA

1550
TTGAGTAGATCTCCGTTTCTATTGCTTGAG 1570           1590
CGTATAAAGGGAAGGCTTGATAGTGCTATA

1610
GCAAAGACTTTTTCTATTCGCAGCGCTAGA 1630           1650
GGCCGGTCTATTTATGATATATTCTCACAG

1670
TCAGAAATTGGAGTGCTGGCTCGTATAAAA 1690           1710

-continued
AAAAGACGAGTAGCGTTCTCTGAGAATCAA

1730
AATTCTTTCTTTGATGGCTTCCCAACAGGA 1750           1770
TACAAGGATATTGATGATAAAGGAGTTATC

1790
TTAGCTAAAGGTAATTTCGTGATTATAGCA 1810           1830
GCTAGACCATCTATAGGGAAAACAGCTTTA

1850
GCTATAGACATGGCGATAAATCTTGCGGTT 1870           1890
ACTCAACAGCGTAGAGTTGGTTTCCTATCA

1910
CTAGAAATGAGCGCAGGTCAAATTGTTGAG 1930           1950
CGGATTATTGCTAATTTAACAGGAATATCT

1970
GGTGAAAAATTACAAAGAGGGGATCTCTCT 1990           2010
AAAGAAGAATTATTCCGAGTAGAAGAAGCT

2030
GGAGAAACGGTTAGAGAATCACATTTTTAT 2050           2070
ATCTGCAGTGATAGTCAGTATAAGCTTAAC

2090
TTAATCGCGAATCAGATCCGGTTGCTGAGA 2110           2130
AAAGAAGATCGAGTAGACGTAATATTTATC

2150
GATTACTTGCAGTTGATCAACTCATCGGTT 2170           2190
GGAGAAAATCGTCAAAATGAAATAGCAGAT

2210
ATATCTAGAACCTTAAGAGGTTTAGCCTCA 2230           2250
GAGCTAAACATTCCTATAGTTTGTTTATCC

2270
CAACTATCTAGAAAAGTTGAGGATAGAGCA 2290           2310
AATAAAGTTCCCATGCTTTCAGATTTGCGA

2330
GACAGCGGTCAAATAGAGCAAGACGCAGAT 2350           2370
GTGATTTTGTTTATCAATAGGAAGGAATCG

2390
TCTTCTAATTGTGAGATAACTGTTGGGAAA 2410           2430
AATAGACATGGATCGGTTTTCTCTTCGGTA

2450
TTACATTTCGATCCAAAAATTAGTAAATTC 2470           2490

```
                            -continued
TCCGCTATTAAAAAAGTATGGTAAATTATA

2510
GTAACTGCCACTTCATCAAAAGTCCTATCC
                ORF2>>

2530            2550
ACCTTGAAAATCAGAAGTTTGGAAGAAGAC

2570
CTGGTCAATCTATTAAGATATCTCCCAAAT 2590            2610
TGGCTCAAAATGGGATGGTAGAAGTTATAG

2630
GTCTTGATTTTCTTTCATCTCATTACCATG 2650            2670
CATTAGCAGCTATCCAAAGATTACTGACCG

2690
CAACGAATTACAAGGGGAACACAAAAGGGG 2710            2730
TTGTTTTATCCAGAGAATCAAATAGTTTTC

2750
AATTTGAAGGATGGATACCAAGAATCCGTT 2770            2790
TAACAAAAACTGAATTCTTAGAGGCTTATG

2810
GAGTTAAGCGGTATAAAACATCCAGAAATA 2830            2850
AGTATGAGTTTAGTGGAAAAGAAGCTGAAA

2870
CTGCTTTAGAAGCCTTATACCATTTAGGAC 2890            2910
ATCAACCGTTTTTAATAGTGGCAACTAGAA

2930
CTCGATGGACTAATGGAACACAAATAGTAG 2950            2970
ACCGTTACCAAACTCTTTCTCCGATCATTA

2990
GGATTTACGAAGGATGGGAAGGTTTAACTG 3010            3030
ACGAAGAAAATATAGATATAGACTTAACAC

3050
CTTTTAATTCACCACCTACACGGAAACATA 3070            3090
AAGGGTTCGTTGTAGAGCCATGTCCTATCT

3110
TGGTAGATCAAATAGAATCCTACTTTGTAA 3130            3150
TCAAGCCTGCAAATGTATACCAAGAAATAA

3170
AAATGCGTTTCCCAAATGCATCAAAGTATG 3190            3210
CTTACACATTTATCGACTGGGTGATTACAG

3230
CAGCTGCGAAAAGAGACGAAAATTAACTA 3250            3270
```
```
                            -continued
AGGATAATTCTTGGCCAGAAAACTTGTTAT

3290
TAAACGTTAACGTTAAAAGTCTTGCATATA 3310            3330
TTTTAAGGATGAATCGGTACATCTGTACAA

3350
GGAACTGGAAAAAAATCGAGTTAGCTATCG 3370            3390
ATAAATGTATAGAAATCGCCATTCAGCTTG

3410
GCTGGTTATCTAGAAGAAAACGCATTGAAT 3430            3450
TTCTGGATTCTTCTAAACTCTCTAAAAAAG

3470
AAATTCTATATCTAAATAAAGAGCGCTTTG 3490            3510
AAGAAATAACTAAGAAATCTAAAGAACAAA

3530
TGGAACAATTAGAACAAGAATCTATTAATT 3550            3570
AATAGCAAGCTTGAAACTAAAAACCTAATT

3590
TATTTAAAGCTCAAAATAAAAAGAGTTTT 3610            3630
AAAATGGGAAATTCTGGTTTTTATTTGTAT

3650
AACACTGAAAACTGCGTCTTTGCTGATAAT
    ORF3 >>
        3670            3690
ATCAAAGTTGGGCAAATGACAGAGCCGCTC

3710
AAGGACCAGCAAATAATCCTTGGGACAACA 3730            3750
TCAACACCTGTCGCAGCCAAAATGACAGCT

3770
TCTGATGGAATATCTTTAACAGTCTCCAAT 3790            3810
AATTCATCAACCAATGCTTCTATTACAATT

3830
GGTTTGGATGCGGAAAAAGCTTACCAGCTT 3850            3870
ATTCTAGAAAAGTTGGGAGATCAAATTCTT

3890
GATGGAATTGCTGATACTATTGTTGATAGT 3910            3930
ACAGTCCAAGATATTTTAGACAAAATCAAA

3950
ACAGACCCTTCTCTAGGTTTGTTGAAAGCT 3970            3990
TTTAACAACTTTCCAATCACTAATAAAATT

4010
CAATGCAACGGGTTATTCACTCCCAGTAAC 4030            4050
```

-continued

ATTGAAACTTTATTAGGAGGAACTGAAATA

4070
GGAAAATTCACAGTCACACCCAAAAGCTCT 4090          4110
GGGAGCATGTTCTTAGTCTCAGCAGATATT

4130
ATTGCATCAAGAATGGAAGGCGGCGTTGTT 4150          4170
CTAGCTTTGGTACGAGAAGGTGATTCTAAG

4190
CCCTGCGCGATTAGTTATGGATACTCATCA 4210          4230
GGCATTCCTAATTTATGTAGTCTAAGAACC

4250
AGTATTACTAATACAGGATTGACTCCGACA 4270          4290
ACGTATTCATTACGTGTAGGCGGTTTAGAA

4310
AGCGGTGTGGTATGGGTTAATGCCCTTTCT 4330          4350
AATGGCAATGATATTTTAGGAATAACAAAT

4370
ACTTCTAATGTATCTTTTTTAGAGGTAATA 4390          4410
CCTCAAACAAACGCTTAAACAATTTTTATT

4430
GGATTTTTCTTATAGGTTTTATATTTAGAG 4450          4470
AAAACAGTTCGAATTACGGGGTTTGTTATG

4490
CAAAATAAAAGAAAAGTGAGGGACGATTTT
              ORF4 >>

4510          4530
ATTAAAATTGTTAAAGATGTGAAAAAAGAT

4550
TTCCCCGAATTAGACCTAAAAATACGAGTA 4570          4590
AACAAGGAAAAAGTAACTTTCTTAAATTCT

4610
CCCTTAGAACTCTACCATAAAAGTGTCTCA 4630          4650
CTAATTCTAGGACTGCTTCAACAAATAGAA

4670
AACTCTTTAGGATTATTCCCAGACTCTCCT 4690          4710
GTTCTTGAAAAATTAGAGGATAACAGTTTA

4730
AAGCTAAAAAGGCTTTGATTATGCTTATC 4750          4770
TTGTCTAGAAAAGACATGTTTTCCAAGGCT

4790
GAATAGACAACTTACTCTAACGTTGGAGTT 4810          4830

-continued

GATTTGCACACCTTAGTTTTTTGCTCTTTT

4850
AAGGGAGGAACTGGAAAAACAACACTTTCT
ORF5 >>

4870          4890
CTAAACGTGGGATGCAACTTGGCCCAATTT

4910
TTAGGGAAAAAAGTGTTACTTGCTGACCTA 4930          4950
GACCCGCAATCCAATTTATCTTCTGGATTG

4970
GGGGCTAGTGTCAGAAGTGACCAAAAAGGC 4990          5010
TTGCACGACATAGTATACACATCAAACGAT

5030
TTAAAATCAATCATTTGCGAAACAAAAAAA 5050          5070
GATAGTGTGGACCTAATTCCTGCATCATTT

5090
TCATCCGAACAGTTTAGAGAATTGGATATT 5110          5130
CATAGAGGACCTAGTAACAACTTAAAGTTA

5150
TTTCTGAATGAGTACTGCGCTCCTTTTTAT 5170          5190
GACATCTGCATAATAGACACTCCACCTAGC

5210
CTAGGAGGGTTAACGAAAGAAGCTTTTGTT 5230          5250
GCAGGAGACAAATTAATTGCTTGTTTAACT

5270
CCAGAACCTTTTTCTATTCTAGGGTTACAA 5290          5310
AAGATACGTGAATTCTTAAGTTCGGTCGGA

5330
AAACCTGAAGAAGAACACATTCTTGGAATA 5350          5370
GCTTTGTCTTTTTGGGATGATCGTAACTCG

5390
ACTAACCAAATGTATATAGACATTATCGAG 5410          5430
TCTATTTACAAAAACAAGCTTTTTTCAACA

5450
AAAATTCGTCGAGATATTTCTCTCAGCCGT 5470          5490
TCTCTTCTTAAAGAAGATTCTGTAGCTAAT

5510
GTCTATCCAAATTCTAGGGCCGCAGAACAT 5530          5550
ATTCTGAAGTTAACGCATGAAATAGCAAAT

5570
ATTTTGCATATCGAATATGAACGAGATTAC 5590          5610

-continued

TCTCAGAGGACAACGTGAACAAACTAAAAA

5630
AAGAAGCGGATGTCTTTTTTAAAAAAAATC
ORF6 >>

5650              5670
AAACTGCCGCTTCTCTAGATTTTAAGAAGA

5690
CGCTTCCCTCCATTGAACTATTCTCAGCAA 5710              5730
CTTTGAATTCTGAGGAAAGTCAGAGTTTGG

5750
ATCGATTATTTTTATCAGAGTCCCAAAACT 5770              5790
ATTCGGATGAAGAATTTTATCAAGAAGACA

5810
TCCTAGCGGTAAAACTGCTTACTGGTCAGA 5830              5850
TAAAATCCATACAGAAGCAACACGTACTTC

5870
TTTTAGGAGAAAAAATCTATAATGCTAGAA 5890              5910
AAATCCTGAGTAAGGATCACTTCTCCTCAA

5930
CAACTTTTTCATCTTGGATAGAGTTAGTTT 5950              5970
TTAGAACTAAGTCTTCTGCTTACAATGCTC

5990
TTGCATATTACGAGCTTTTTATAAACCTCC 6010              6030
CCAACCAAACTCTACAAAAAGAGTTTCAAT

6050
CGATCCCCTATAAATCCGCATATATTTGG 6070              6090
CCGCTAGAAAAGGCGATTTAAAAACCAAGG

6110
TCGATGTGATAGGGAAAGTATGTGGAATGT 6130              6150
CGAACTCATCGGCGATAAGGGTGTTGGATC

6170
AATTTCTTCCTTCATCTAGAAACAAAGACG 6190              6210
TTAGAGAAACGATAGATAAGTCTGATTCAG

6230
AGAAGAATCGCCAATTATCTGATTTCTTAA 6250              6270
TAGAGATACTTCGCATCATGTGTTCCGGAG

6290
TTTCTTTGTCCTCCTATAACGAAAATCTTC 6310              6330
TACAACAGCTTTTTGAACTTTTTAAGCAAA

6350
AGAGCTGATCCTCCGTCAGCTCATATATAT 6370              6390

-continued

ATATCTATTATATATATATATTTAGGGATT

6410
TGATTTCACGAGAGATTTGCAACTCTTG 6430              6450
GTGGTAGACTTTGCAACTCTTGGTGGTAGA

6470
CTTTGCAACTCTTGGTGGTAGACTTTGCAA 6490              6510
CTCTTGGTGGTAGACTTGGTCATAATGGAC

6530
TTTTGTTAAAAAATTTATTAAAATCTTAGA 6550              6570
GCTCCGATTTTGAATAGCTTTGGTTAAGAA

6590
AATGGGCTCGATGGCTTTCCATAAAAGTAG
ORF7 >>

6610              6630
ATTGTTTTTAACTTTTGGGGACGCGTCGGA

6650
AATTTGGTTATCTACTTTATCTTATCTAAC 6670              6690
TAGAAAAAATTATGCGTCTGGGATTAACTT

6710
TCTTGTTTCTTTAGAGATTCTGGATTTATC 6730              6750
GGAAACCTTGATAAAGGCTATTTCTCTTGA

6770
CCACAGCGAATCTTTGTTTAAAATCAAGTC 6790              6810
TCTAGATGTTTTAATGGAAAAGTTGTTTC

6830
AGAGGCATCTAAACAGGCTAGAGCGGCATG 6850              6870
CTACATATCTTTCACAAAGTTTTTGTATAG

6890
ATTGACCAAGGGATATATTAAACCCGCTAT 6910              6930
TCCATTGAAAGATTTTGGAAACACTACATT

6950
TTTTAAAATCCGAGACAAAATCAAAACAGA 6970              6990
ATCGATTTCTAAGCAGGAATGGACAGTTTT

7010
TTTTGAAGCGCTCCGGATAGTGAATTATAG 7030              7050
AGACTATTTAATCGGTAAATTGATTGTACA

7070
AGGGATCCGTAAGTTAGACGAAATTTTGTC 7090              7110
TTTGCGCACAGACGATCTATTTTTTGCATC

7130
CAATCAGATTTCCTTTCGCATTAAAAAAAG 7150              7170

-continued

```
ACAGAATAAAGAAACCAAAATTCTAATCAC

7190
ATTTCCTATCAGCTTAATGGAAGAGTTGCA 7210            7230
AAAATACACTTGTGGGAGAAATGGGAGAGT

7250
ATTTGTTTCTAAAATAGGGATTCCTGTAAC 7270            7290
AACAAGTCAGGTTGCGCATAATTTTAGGCT

7310
TGCAGAGTTCCATAGTGCTATGAAAATAAA 7330            7350
AATTACTCCCAGAGTACTTCGTGCAAGCGC

7370
TTTGATTCATTTAAAGCAAATAGGATTAAA 7390            7410
AGATGAGGAAATCATGCGTATTTCCTGTCT

7430
TTCATCGAGACAAAGTGTGTGTTCTTATTG 7450            7470
TTCTGGGGAAGAGGTAATTCCTCTAGTACA

7490
AACACCCACAATATTGTGATATAATTAAAA
```

-continued

```
TT.
```

2. An isolated ORF3 gene comprising the nucleotide sequence 3604 through 4398, SEQ ID NO:11, according to claim 1.

3. An isolated ORF4 gene comprising the nucleotide sequence 4468 through 4773, SEQ ID NO:3, according to claim 1.

4. A recombinant expression vector comprising the ORF3 of claim 2.

5. A recombinant expression vector comprising the ORF4 of claim 3.

6. *Escherichia coli* transformed by the expression vector of claim 4.

7. *Escherichia coli* transformed by the expression vector of claim 5.

8. A recombinant expression vector comprising at least one gene selected from the group consisting of ORF3 comprising the nucleotide sequence 3604 through 4398, SEQ ID NO:11 and ORF4 comprising the nucleotide sequence 4468 through 4776, SEQ ID NO:13, as set forth in claim 1.

9. *Escherichia coli* transformed by the expression vector of claim 8.

* * * * *

UNITED STATES PATENT AND TRADEMARK OFFICE
CERTIFICATE OF CORRECTION

PATENT NO.    : 6,248,563 B1
DATED         : June 19, 2001
INVENTOR(S)   : Rattii et al.

It is certified that error appears in the above-identified patent and that said Letters Patent is hereby corrected as shown below:

Column 1,
Line 5, please delete "444,185" and insert therefor -- 444,189 --;
Line 13, please delete "PCTD" and insert therefor -- pCTD --;

Column 2,
Lines 23 and 60, please delete "PCTD" and insert therefor -- pCTD --;

Column 5,
Line 24, please delete "Centricon" and insert therefor -- Centricon® --;

Column 7,
Line 3, please delete "uml" and insert therefore -- $\mu$ml --.

Signed and Sealed this

Eighth Day of July, 2003

JAMES E. ROGAN
*Director of the United States Patent and Trademark Office*